(12) United States Patent
Bennett et al.

(10) Patent No.: US 8,679,014 B2
(45) Date of Patent: Mar. 25, 2014

(54) NETWORK SUPPORTING INTRAVAGINAL MONITORING DEVICE

(76) Inventors: James D. Bennett, Hroznetin (CZ);
Witold Andrew Ziarno, Thalheim (DE)

( * ) Notice: Subject to any disclaimer, the term of this patent is extended or adjusted under 35 U.S.C. 154(b) by 430 days.

(21) Appl. No.: 12/890,750

(22) Filed: Sep. 27, 2010

(65) Prior Publication Data
US 2011/0190595 A1  Aug. 4, 2011

Related U.S. Application Data

(60) Provisional application No. 61/246,375, filed on Sep. 28, 2009, provisional application No. 61/246,405, filed on Sep. 28, 2009, provisional application No. 61/246,396, filed on Sep. 28, 2009, provisional application No. 61/290,792, filed on Dec. 29, 2009, provisional application No. 61/263,416, filed on Nov. 23, 2009.

(51) Int. Cl.
*A61B 5/00* (2006.01)
*G06F 19/00* (2011.01)

(52) U.S. Cl.
CPC .................................. *G06F 19/34* (2013.01)
USPC ........................... 600/301; 600/135; 600/591

(58) Field of Classification Search
USPC .................. 600/135, 300, 301, 591; 607/318
See application file for complete search history.

(56) References Cited

U.S. PATENT DOCUMENTS

| | | | |
|---|---|---|---|
| 5,096,830 A | 3/1992 | Senyei et al. | |
| 6,200,279 B1 | 3/2001 | Paltieli | |
| 6,450,977 B1 | 9/2002 | Baxter-Jones | |
| 6,669,653 B2 | 12/2003 | Paltieli | |
| 6,741,895 B1 | 5/2004 | Gafni et al. | |
| 6,896,653 B1 | 5/2005 | Vail, III et al. | |
| 6,994,678 B2 | 2/2006 | Baxter-Jones et al. | |
| 7,154,398 B2 * | 12/2006 | Chen et al. ................ | 340/573.1 |
| 7,207,941 B2 * | 4/2007 | Sharf ............................. | 600/438 |
| 7,628,744 B2 * | 12/2009 | Hoffman et al. ............. | 482/148 |
| 7,850,625 B2 | 12/2010 | Paltieli et al. | |
| 7,937,249 B2 * | 5/2011 | Osborn et al. .................... | 703/2 |
| 2002/0198473 A1 * | 12/2002 | Kumar et al. ................. | 600/595 |
| 2005/0049509 A1 * | 3/2005 | Mansour et al. ............. | 600/476 |
| 2005/0203399 A1 | 9/2005 | Vaezy et al. | |
| 2005/0267377 A1 * | 12/2005 | Marossero et al. ........... | 600/511 |
| 2006/0149597 A1 | 7/2006 | Powell et al. | |
| 2007/0112284 A1 * | 5/2007 | Hoffman et al. ............. | 600/591 |
| 2008/0071190 A1 * | 3/2008 | Gorodeski et al. ........... | 600/551 |
| 2008/0146887 A1 * | 6/2008 | Rao et al. ..................... | 600/300 |
| 2009/0076368 A1 * | 3/2009 | Balas ........................... | 600/407 |
| 2009/0143646 A1 * | 6/2009 | Vail, III ........................ | 600/135 |
| 2009/0185096 A1 | 7/2009 | Park | |

(Continued)

FOREIGN PATENT DOCUMENTS

| | | |
|---|---|---|
| CA | 2 608 497 | 8/2006 |
| CN | 101194278 | 6/2008 |

(Continued)

*Primary Examiner* — Bill Thomson
*Assistant Examiner* — Bobby Soriano
(74) *Attorney, Agent, or Firm* — Da Vinci Partners LLC; John Moetteli

(57) ABSTRACT

The invention generally relates to intravaginal monitoring devices, supporting networks, web services, billing services, modes of operation of the devices and networks, and processing of data harvested by an intravaginal device and communication to the network. Methods, systems and networks for advertising are provided herein.

20 Claims, 21 Drawing Sheets

(56) References Cited

U.S. PATENT DOCUMENTS

| | | | |
|---|---|---|---|
| 2009/0222058 A1* | 9/2009 | Craggs | 607/41 |
| 2009/0281397 A1* | 11/2009 | Lavoisier | 600/301 |
| 2010/0009336 A1* | 1/2010 | Sullivan | 435/3 |
| 2010/0016668 A1* | 1/2010 | Gal | 600/135 |
| 2010/0036279 A1* | 2/2010 | Rieth | 600/551 |
| 2010/0081895 A1* | 4/2010 | Zand | 600/309 |
| 2010/0235782 A1 | 9/2010 | Powell et al. | |

FOREIGN PATENT DOCUMENTS

| | | |
|---|---|---|
| WO | WO 2006/086089 | 8/2006 |
| WO | WO 2010/105063 | 9/2010 |
| WO | WO 2010/144413 | 12/2010 |

\* cited by examiner

IMD Support Server (www.imdsupport.com) 1421

Home | About | Contact Us | FAQ 1451

*USER DATA [Ms. ABC]* 1441

Language: 1445
English  1449

| Date/Time | File Name | Sensor Readings | Recommendations From Doctor |
|---|---|---|---|
| | | | |
| | | | |

Patient's Database 1497

Upload: 1455
Browse  1457

Go To Date: 1459
20 | SEPT | 2009  1461

Image Window: 1463
1465

Image Display 1411

Use Upload Button to Upload Files. Select Date/Time and File Name to View Images. 1493

Done

Client's Browser 1495

NETWORK SUPPORTING INTRAVAGINAL MONITORING DEVICE

CROSS REFERENCES TO RELATED APPLICATIONS

This application incorporates by reference herein in their entirety and makes reference to, claims priority to, and claims the benefit of:

a) U.S. Provisional Application Ser. No. 61/246,375 filed Sep. 28, 2009, entitled "Intravaginal Monitoring Device" by Ziarno et al.;

b) U.S. Provisional Application Ser. No. 61/246,405 filed Sep. 28, 2009, entitled "Network Supporting Intravaginal Monitoring Device, Method and Post Harvesting Processing of Intravaginally Processed Data" by Ziarno et al.;

c) U.S. Provisional Application Ser. No. 61/246,396 filed Sep. 28, 2009, entitled "Network Supporting Intravaginal Monitoring Device" by Ziarno et al.

d) U.S. Provisional Application Ser. No. 61/290,792 filed Dec. 30, 2009, entitled "Network Supporting Intravaginal Monitoring Device, Method and Post Harvesting Processing of Intravaginally Processed Data" by Ziarno et al.; and e) U.S. Provisional Application Ser. No. 61/263,416 filed Nov. 23, 2009, entitled "Intravaginal Monitoring Architecture" by Ziarno et al.

Also incorporated herein by reference in their entirety are:

a) U.S. patent application Ser. No. 12/890,743 filed on even date herewith by Ziarno et al., entitled "Intravaginal Monitoring Device";

b) U.S. patent application Ser. No. 12/890,750 filed on even date herewith by Bennett et al., entitled "Network Supporting Intravaginal Monitoring Device";

c) U.S. patent application Ser. No. 12/890,764 filed on even date herewith by Bennett et al., entitled "Analysis Engine within a Network Supporting Intravaginal Monitoring";

d) U.S. patent application Ser. No. 12/890,805 filed on even date herewith by Bennett et aL, entitled "Intravaginal Monitoring Support Architecture";

e) U.S. patent application Ser. No. 12/890,811 filed on even date herewith by Bennett et al., entitled "Intravaginal Therapy Device";

f) U.S. patent application Ser. No. 12/890,830 filed on even date herewith by Bennett et al., entitled "intravaginal Dimensioning System"; and g) U.S. patent application Ser. No. 12/890,847 filed on even date herewith by Bennett et al., entitled "Intravaginal Optics Targeting System"; and h) PCT Patent Application Ser. No. PCT/US10/50329 filed on even date herewith by Bennett et al., entitled "Intravaginal Monitoring Device and Network".

BACKGROUND

1. Technical Field

The invention generally relates to medical devices and more particularly to medical devices used in the obstetrics and or gynecology sector, supporting networks, modes of operation of the devices and networks, and processing of data harvested by an intravaginal device and communication to the network.

2. Related Art

The prior art does not provide for a way for a woman to readily know about the status of her reproductive health from the comfort of her own home. Moreover, the prior art does not provide a way to easily obtain information related to: pregnancy, the onset of sexually transmitted diseases, fertility, premature birthing conditions, labor, the timing of estrus in animals, and the development of pre-cancerous or cancerous conditions.

These and other limitations and deficiencies associated with the related art may he more fully appreciated by those skilled in the art after comparing such related art with various aspects of the present invention as set forth herein with reference to the figures.

BRIEF SUMMARY OF THE INVENTION

The present invention is directed to apparatus and methods of operation that are further described in the following Brief Description of the Drawings, the Detailed Description of the Invention, and the claims. Other features and advantages of the present invention will become apparent from the following detailed description of the invention made with reference to the accompanying drawings.

BRIEF DESCRIPTION OF THE DRAWINGS

FIG. 14 is a schematic diagram illustrating an exemplary snapshot of the web browser page provided to the patient or user, by the external servers of the FIG. 11;

FIG. 15 is a schematic diagram illustrating an exemplary snapshot of the web browser page provided to the regionally or remotely located healthcare professionals, by the external servers of the FIG. 11, via the regional and remote healthcare professional servers of the FIG. 12;

DETAILED DESCRIPTION OF THE DRAWINGS

Figure 1:
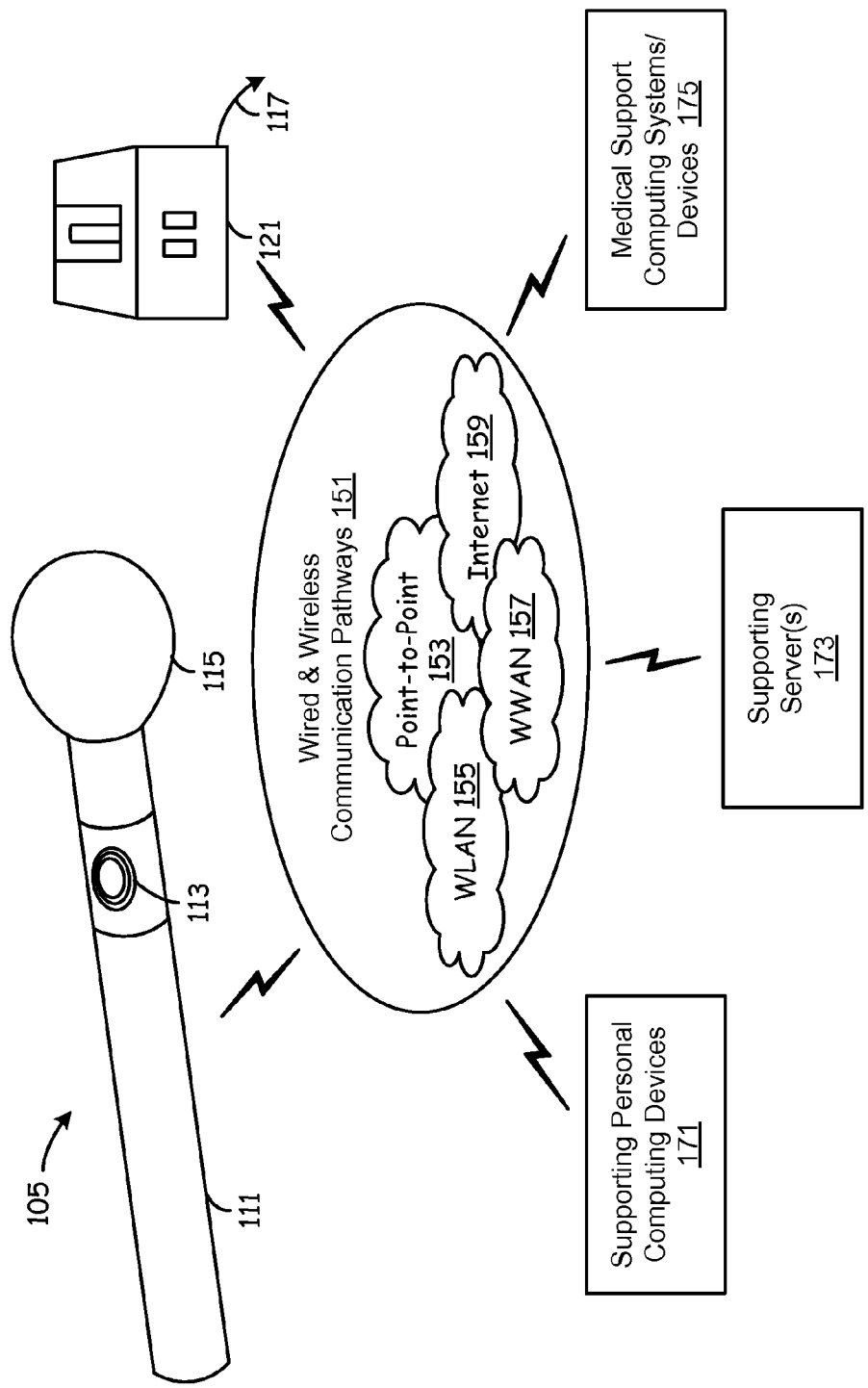
FIG. 1 is a schematic block diagram illustrating a supporting network infrastructure for an intravaginal monitoring device; wherein the intravaginal monitoring device communicates via a communication interface to external devices and/or external servers via wired and/or wireless network pathways.

FIG. 1 is a schematic block diagram illustrating a supporting network infrastructure for an intravaginal monitoring device 105; wherein the intravaginal monitoring device 105 communicates via a communication interface 121, 117 to external devices 171 and/or external servers 173, 175 via wired and/or wireless network pathways. In specific, the intravaginal monitoring device 105, consisting of a cap or bulb 115, a stem 111 and an on/off switch 133 (at the bare minimum levels of electronics), has (dedicated) wired/wireless communication interfaces 121, 117 that enables the intravaginal monitoring device 105 to communicate with external devices 171 (or, supporting personal computing devices) and servers 173, 175 (in specific,—dedicated—supporting servers 173 and medical support computing systems/devices 175). Moreover, this communication occurs via wired/wireless communication pathways 151 that may easily include point-to-point 153, WLAN (Wireless Local Area Network) 155, WWAN (Wireless Wide Area Network) 157, and Internet 159. As is appreciated, housing of device 115 in another variant, can be molded or formed from a single material, e.g. medical grade silicon, glass, e.g. pyrex™, a medical grade plastic, acrylic, or other suitable biocompatible material. In this variant, an optionally removable electronics unit is mounted in a channel with the housing which also optionally includes free space or hollow space between the electronics unit and the very top of the head of device.

The intravaginal monitoring device 105, via the communication interfaces 121, 117, is able to initially communicate with supporting personal computing devices 171 (which are located in the vicinity of the female user) or other consumer wireless enabled device, e.g. smart phone, mobile phone, iPod, camera, printer, laptop computer, netbook, PC, dedicated remote device, or another intravaginal device. These supporting personal computing devices 171 also include cell phones and personal computers, or simply an access point, for instance. The intravaginal monitoring device 105, while inserted in place (inside the vaginal channel) or after usage and removal, allows an authenticated supporting personal computing device 171 to send control signals (as well as firmware and other logistical program codes) and receive images/video clips/sensor data and so forth from the intravaginal monitoring device 105. Similarly device 105 sends control signals to other remote devices it is communicatively linked to as well as status of intravaginal device information, information related to data stored on the intravaginal device, information regarding the functioning of the intravaginal device, data regarding the remaining unused storage on the intravaginal device, data identifying the device itself, e.g. serial number, purchaser, etc.

The communication, alternatively, may also be initiated by the intravaginal monitoring device 105, upon removal from the vaginal channel, upon switching off the intravaginal monitoring device 105, upon memory full, upon emergency situations, and upon communication button press (if there exists one) by the user. These logistical codes are built into the intravaginal monitoring device 105; however, they might also be received from supporting servers 173, by request. The receiving of images/video clips/sensor data is also initiated remotely by supporting servers 173 (as per certain logistics) or medical support systems/devices 175 (as per a healthcare professional's instructions, for instance).

For instance, a female user may purchase a intravaginal monitoring device 105 kit, consisting of intravaginal monitoring device 105 as well as a dock where the intravaginal monitoring device 105 is placed for charging and for communications (alternatively, communication may also occur while in vaginal channel). The female user may also sign up with supporting server 173 and in addition may also sign up for service from local/regional/remote healthcare professionals (which is possible via the very same supporting server 173). The female user enters personal information on a remote device or on intravaginal device, e.g. data regarding feelings, emotions, the state of her body, e.g. changes related to her menstrual cycle, data regarding sex partners, including names, addresses, dates of coitus, data regarding abnormal or normal feelings and or pain in parts of her anatomy, data of her healthcare providers, data related to insurance coverage or lack thereof, data regarding clinics she is receiving treatment in, data regarding her location at select points in time, data regarding surgical procedures, data regarding drugs she is taking or has taken, data related to movements of a being within her womb, data regarding ovulation changes in her body, data regarding visible symptoms related to an STD, etc. This data is communicated to server 173 in one variant, and stored at a storage device communicating with server 173. It is appreciated that a method and network for archiving is provided where a female can store her sexual history, and the data referenced above. This archival data is compared with data harvested using the intravaginal device at another point in time. Tracking of the condition of the female's cervix is provided, as well as changes over time are identified, which are normal in one variant or are abnormal in another variant. Tracking enables the identification of the date and time where changes are observed and recorded. Where the changes are related to sexual activity, a record is provided to identify the source of the change, e.g. infected sex partner. Where the changes are due to other sources, e.g. the formation of precancerous or cancerous changes, a specific date and time for these changes is then identified. As such, an appropriate therapy is provided to cure or treat the symptoms related to the changes. Alerts or notifications are selectively also sent from server 173 to remote device of the female, of the physician, a hospital electronic record processing system, and the like. Server 173 or associated computing system compares archivally harvested data with new data transferred thereto. Various software or firmware modules are present on server 173 or a device communicatively linked thereto. The modules process the archival data and new data and determine if a clinically relevant change is manifest in the new data. If there is a clinically relevant change is detected, the change is flagged, and alerts or notifications are communicated out onto various nodes on the network. If there are no clinically relevant changes detected, optionally an alert to that effect is also communicated out onto various nodes on the network. In another variant, the modules have a filtering mode of functionality. It is appreciated that vast amounts of data, in one variant, are communicated from a multiplicity of intravaginal units to one or more servers 173 or other network nodes. This data is processed and filtered using a filtering mode of operation so that only clinically relevant data is transferred and or stored, while, optionally, non relevant data is overwritten or otherwise disgarded.

In another variant, server 173 or other network node includes a select service mode of operation, which provides various functionalities on device 115. A menu of service functionality or analysis regimes is provided. A menu is provided on a web site and or web pages. The menu is provided to a medical professional, purchaser of the intravaginal device or user of the intravaginal device for the individual to select device functionality. For example, the menu includes an STD detection mode of operation and or service, an ovulation detection mode of operation or service, a rhythm method (infertility) mode of operation or service, a precancerous tissue monitoring or service, a general cervix monitoring mode of operation, an infection mode of operation and or service, a pregnancy mode of operation and or service, a cervical incompetence monitoring mode of operation and or service, a physician registry mode of operation and or service, a birthing center mode of operation and or service, an nearest available appointment (e.g. time and location) mode of operation and or service, a clinical practice mode of operation or service that permits a doctor's or doctor's practice group to receive data from multiple intravaginal devices to monitor patient's, a birthing center patient management mode of operation and or service that permits a birthing center to receive data from a multiplicity of remote intravaginal devices and manage admissions for patients, an advertiser mode of operation and or service that permits the user to select or deselect receipt of advertising, an available therapy mode of operation and or service that permits a user or other party to receive information on current therapies for gynecological or obstetrics abnormalities and or conditions. Of course, other general modes of operation are also provided herein that assist in physician time management by providing a physician with patient status data, electronic medical record information, information harvested by other medical devices that bear on the therapy or patient.

In yet another variant, one or more nodes on the network at a specialty treatment center, e.g. a high risk regional birthing center with special expertise, receive data harvested from a plurality of remotely located intravaginal devices related to conditions or events. It is appreciated that this mode of operation and or service provision permits females who are in locations with little or poor medical expertise to be diagnosed, and therapy managed remotely.

In yet another variant, a post treatment or therapy mode of monitoring is provided herein. In this mode, a female uses the device, the data gets transferred to server 173 or other network node, and the course of a drug therapy, surgical intervention post surgery, or other therapy is communicated on other remote devices on the network.

In yet another variant, the intravaginal device, and web service, forms part of a kit where the other kit members include, one or more of the following, alone or in combination: a cell phone, baby products, a drug, a fertility drug, a birth control therapy, another medical device, a device used for birth control, e.g. an IUD, birth control pills, clothing, a smart phone, a gift certificate, a free subscription to a web service related to the intravaginal device and or unrelated thereto, a free sample, a free sample of a woman's hygiene product, a tampon, a vitamin, a nutritional supplement, a pregnancy nutritional supplement, a treatment for an STD.

Then, to use the intravaginal monitoring device 105, the female user follows the instructions provided within the intravaginal monitoring device 105 kit and or receives instruction from a medical professional on its use, from the supporting servers 173 and/or medical support computing systems/devices 175 (via the healthcare professionals from whom the female user has requested service). The instructions are streamlined for various specific circumstances that include routine checkups, menstrual cycles, menopause, sexually transmitted diseases and pregnancy checkups (may also include pre and/or post coitus periods). In another variant, the service or mode of operation of the device includes a routine check up mode of operation or service. As is appreciated, that for normal healthy woman use of the device and web service is used in a method of female health monitoring in conjunction with physical examinations by physicians or other medical professionals as well as an adjunct thereto. By way of example, between routine check ups in the medical professionals office the intravaginal device is used via the servers and network and other nodes on the network to provide between visit monitoring. By way of further example, where a female is showing the first or early symptoms of cervical incompetence, the female is generally placed on a therapy that includes bed rest to reduce pressure on the cervix and monitored weekly with a physical examination. In many situations, the cervical incompetence condition worsens between doctor's visits notwithstanding the bed rest therapy. As such, the intravaginal device is an adjunct to this therapy and provides the medical professional by way of the network of the invention to provide real-time monitoring of the patient between visits.

The intravaginal device, and network described herein is also used to monitor and track events related to Spontaneous abortion (SAB), or miscarriage. SAB is the term used for a pregnancy that ends on it's own, within the first 20 weeks of gestation. Miscarriage is the most common type of pregnancy loss, anywhere from 10-25% of all clinically recognized pregnancies will end in miscarriage. It is appreciated that the intravaginal device along with the network and nodes detects and processes bleeding data that may occur around the time of female's expected period. Similarly, most miscarriages occur during the first 13 weeks of pregnancy and the device and network described herein have a mode of operation of operation that detects and processes events during this period of time. During the first trimester, the most common cause of miscarriage is chromosomal abnormality—meaning that something is not correct with the being in the womb's chromosomes. Most chromosomal abnormalities are the cause of a faulty egg or sperm cell DNA, or are due to a problem at the time that the zygote went through the division processes. It is appreciated that the intravaginal device and the network described herein are used to identify the events associated with a miscarriage, including providing a historical record of data from the preconception stage, to the conception stage, through the pregnancy stage, all the way through the event of miscarriage and all the way through post miscarriage. For human females in childbearing years, the risk of having a miscarriage ranges from 10-25%, and in most healthy human females the average is about a 15-20% chance. It is known that an increase in maternal age affects the chances of miscarriage, females under the age of 35 yrs old have about a 15% chance of miscarriage. Females who are in the range of 35-45 yrs of age have a 20-35% chance, while females over the age of 45 can have a significant risk going as high as 50%. Moreover, a female who has had a previous miscarriage has a 25% chance of having another. The intravaginal device and network of the present invention enables the harvesting of event data associated with a miscarriage.

In another variant, a module, e.g. a web page entry and associated software, enables a user or medical profession to log symptoms, which include mild to severe back pain, weight loss. Similarly, the device and network harvest, process and record intravaginal data and events that include white-pink mucus discharge, true contractions brown or bright red bleeding with or without cramps, tissue with clot like material passing from the cervix, and monitor other signs of pregnancy and the loss thereof. As miscarriage involves a process and stages all of these are monitored using the device and network of the present invention in one mode of operation. For example, in threatened miscarriage, the device harvests data and the network processes data that includes early pregnancy uterine bleeding, and information regarding cramping or lower backache is entered onto the network. Data captured by the intravaginal may indicate a closed cervix. Another mode of operation of the device and network includes processing data related to incomplete miscarriage. Abdominal or back pain data entered into the system, and the device harvests bleeding data along with data associated with an open cervix. An alert is sent that miscarriage may be inevitable when there is harvesting of dilation data and or effacement of the cervix data, and/or data indicative of a rupture of the membranes. Continued bleeding data is recorded by the device, and cramping data is entered onto the network. As such an accurate timeline for the process is created.

In another variant, the device and network of the present invention includes a mode of operation for capturing and processing data associated with a completed miscarriage. A completed miscarriage occurs when the embryo or products of conception have emptied out of the uterus, through the cervix. The device captures and or nodes on the network process and record this data. Bleeding data including periodicity is captured, and pain or cramping data is entered on nodes on the network, e.g. a cellphone with appropriate user GUI. The data from the device and system, are optionally used in combination, with an ultrasound test to confirm the completed miscarriage.

As is appreciated the device and network includes a mode of operation that monitors, processes and tracks event data indicative of a missed miscarriage. Females may experience a miscarriage without realizing it. A missed miscarriage involves embryonic deal, but there may not be any expulsion of the embryo from the uterus through the cervix. In this mode of operation the device and network harvests, processes and records data that include loss of pregnancy symptoms. In particular, the sensors on the device harvest data that is indicative of the absence of fetal heart tones. This is then optionally confirmed with an ultrasound test or devices.

Where a couple is continually trying to have a child, the device and network are used to harvest and monitor events associated with recurrent miscarriage in another mode of operation. By way of example, an anembryonic pregnancy mode of operation is also provided. In this mode of operation, a fertilized egg implants into the uterine wall, but fetal development never progresses. In many situations, a gestational sac with or without a yolk sac is formed, but there is an absence of fetal development. Events and data associated with the gestational sac through the cervical canal are harvested by the intravaginal device.

Data processed by the intravaginal device and network, are used in combination with therapies for miscarriage. By way of example, these include treatments to prevent hemorrhaging and/or infection. Where the body does not expel all the newly formed tissue (the intravaginal device and the network have a record of no events that indicate explusio, a dilation and curettage therapy is provided. Moreover, drugs are prescribed to help control bleeding after the therapy is administered. The device and network is used in a bleeding monitoring mode of operation once the subject returns home; if data that indicates an increase in bleeding or data is entered on nodes of the network, e.g. the onset of chills or fever, one or more nodes on the network send an alert out to the medical professional and the user indicating that consultation and or admission to a healthcare facility is necessary.

In another variant, a web site associated with the presentation of data (the actual site or hyperlink thereto also include modes of operation that assist the user to find an OBGYN, find a midwife, find an infertility specialist, find a genetic counselor, and or find links to find emotional support from other pregnant women or professional counselors.

In yet another variant, the intravaginal device and network are used in combination with assisted reproductive therapies (ART), to provide an improved method and system for getting pregnant. These therapies include procedures in which eggs are surgically removed from a female's ovaries and combined with sperm to assist a female to achieve pregnancy. These therapies include in vitro fertilization (IVF), gamete intrafallopian transfer (GIFT), and or zygote intrafallopian transfer (ZIFT). The device, method and network are used in the ART therapies which include, in combination with device data harvest, an ART procedure, ovarian stimulation, and or the use of frozen embryos that are thawed for transfer into the female. The method also includes the use of fertility drugs and tests that monitor the female's ovaries for follicle production. In another variant, the device and network are used in an ART cycle which utilizes more than one ART procedure, which include, for example combination cycles combining IVF with either GIFT or ZIFT.

In the ART example, the device and network is used to harvest and process data associated with the concentration of motile sperm. This data is used to determine the causes of infertility, e.g. is there an abnormality with the man or woman. Hence, it is appreciated that the device and network herein can measure in vivo, e.g. after coitus, the concentration of motile sperm that has been spewed into the woman, along with indicating then the most favorable days for the sperm deposit are to increase the likelihood of pregnancy. Of course, the device and method described herein are also used with intrauterine insemination therapies that involve placing the sperm into the female's uterus to increase the chance of pregnancy, and also in multiple fetus pregnancies, e.g. the devices harvest data from multiple being in womb beating hearts, as well as in the scenario involving a stillbirth, where fetal death that occurs after 20 weeks gestation.

In the event of a normal pregnancy, the device, method and network are used to harvest and track data related to early signs of pregnancy. By way of example, data related to a delayed or missed menstrual cycle is entered into the system either by the device or at another mode on the network. Implantation bleeding data is harvested by the device and processed thereat or at some other node on the network as it is one of the earliest symptoms of pregnancy in some females. Normally, 6-12 days after conception, the embryo implants itself into the uterine wall. The device and network nodes track and record spotting data as well as some cramping data, and correlate this information.

In another variant, the device, network and method includes a mode of use and operation that includes optional confirmational tests for pregnancy. In the scenario, where women bleed while they are pregnant, there is a mode of operation that compares and analyzes the period of time the bleeding occurs or quantifies the amount of bleeding to assist in the determination of the status of the pregnancy.

It is appreciated that other physiological symptoms of pregnancy are also entered into various nodes on the system, to provide a complete history of events. By way of example, one or more of the following data are entered onto the system, which may take the format of a menu or check boxes indicating the presence or absence of a certain system: data indicating swollen or tender, fatigue, nausea or morning sickness data, data associated with color changes of the cervix due to hormonal elevations, lower backache symptom data, dull backache data, headache data, urination frequency data (in this variant the device optionally includes an appendage that can automatically monitor urination periodicity), color of the areolas data, darkening of the areolas data, food craving data, other pregnancy symptom data, non pregnancy symptom data, and or other cause data.

As is appreciated, the mode of operation for preterm labor monitoring for the device and network is also provided. In other mode of operation, the device, network and method are used to calculate gestation, conception and due dates accurately using data harvested from the intravaginal device as well as data entered onto one or modes of the network. Some moms can feel their babies move as early as 13-16 weeks from the start of their last period. These first fetal movements are called quickening and are often described as flutters. It may be difficult to determine whether this feeling is gas or your baby's movements, but soon you will begin to notice a pattern. First-time moms may not feel these movements as early as second-time moms. Some moms, especially those in their first pregnancy, may not feel movement until 18-20 weeks. Remember that each woman and each pregnancy is different, so you may not feel movement as early as another woman. There is a broad range of when the first detection of movement can be felt, ranging from 13-25 weeks.

It is understood that the intravaginal device, network and system include a mode of operation to harvest, process and track data concerning the being in the womb using the camera and or other sensors. As the being in the womb develops, it will stretch and flex its limbs. As the pregnancy proceeds being in womb, movement data is collected, as well as intensity data which becomes more pronounced as the pregnancy proceeds, including kicking movements, punching movements, and rolling movements. The movement may also be responsive to external stimulus such as noise or the emotional state of the female, e.g. this data is also recorded on one or more nodes of the network, and a timeline of the child's internal movement activity is correlated with external data or logs of external data. In another variant, the device, system and network are used to track the being in wombs sleeping/waking cycles.

The device, network and modes of operation provide for a convenient method to track the movements of the being in the womb, e.g. as evidenced by sensor measurements. By way of example, beginning at week 28 (or earlier or later), the intravaginal device enters a mode of operation that counts and tracks the being in wombs movements, and their periodicity and or intensity. This data is used by one or more nodes of the network or the device identify potential problems. One or more nodes on the network present a kick or movement count chart, which is optionally printed.

In the event of a pregnancy complication, the device, nodes on the network are used to track and provide alerts if there is a significant deviation in an early pattern of movement, or if there has been no movement at all. For example, there is an alert sent where the movements of the being in womb decrease to fewer than 10 movements within a two hour period of time.

Various forms of data are harvested automatically by the intravaginal device or entered onto one or more nodes of the network in one mode of operation, and processed to provide a prebirth timeline, and to provide a prediction as to the timing of the birthing event: data is entered on the system indicating dropping of the baby, data regarding frequency of urination, data of a bloody show, data of a loss of a mucus plug, data of cervix thinning and relaxation, data of the mucus plug ejection or stringiness of the mucus or discharge, data of the color of the mucus plug, e.g clear, pink or blood tinged, time stamp data surrounding the discharge of the mucus plug, data on rupture of the membranes, data related to amniotic sac breakage and or leakage, data related to the color of the amniotic fluid (e.g. if green and foul smelling there could be sign of infection), effacement of cervix data, data on thickness of the cervix, data on effacement percentages, data on Braxton Hick contractions, data on practice contractions, cervical dilation data, opening of the cervix data, measurement of dilation of the cervix in centimeters, data on consistent contractions, data on regular and or irregular contractions, data regarding the exact time a contraction begins, data regarding the length of a contraction, spacing of individual contractions, intervals of time between contractions, data of contractions that initiate an alert or notification sequence to other devices on the network, labor data contractions, regularness of contractions, data of predictable patterns of contractions, e.g. such as every seven minutes, data of the closeness of contractions one to another, data of the length of contractions in comparison to each other, data of the strength of contractions one to another, data regarding the location of the contraction in the lower back with radiation around the front or vice versa, data regarding changes in activity or position that do not slow down or stop contractions, data of a bloody show, and data of membrane rupture, alone or in combination. Various modes of operation are used to properly harvest this data and process it. Once processed appropriate graphs and charts are prepared, as well as predictions on timing of future events based upon statistical data or personal specific data, e.g. a previous pregnancy.

In another variant of the invention a mode of operation is provided based on harvested data, that provides a false labor vs. true labor discriminator, e.g. software or firmware algorithms. Based upon the conclusions of the discriminator various alerts are sent to nodes on the network providing alerts, instruction data, and so on. As the estimated time of delivery approaches, the female may notice that Braxton Hicks contractions become more frequent and intense. In this scenario, the female or her partner may think that that they are experiencing true labor. Needless hospital visits are made as a result of false labor events. The device, method and nodes on the network process contraction data and provide alerts or notifications the user or doctor with information as to whether real labor events or false labor events are occurring. It is appreciated that this can occur in realtime to various nodes on the network, e.g. the data is fed in realtime, analysis of the data are fed in realtime to varying nodes on the network, alone or in combination. By way of example and in one variant, the false labor vs true labor discriminator shall determine based upon harvest data if the contractions are irregular and unpredictable (for example, in intervals of ten minutes, six minutes, two minutes, eight minutes, etc.), if there is a progression seen over time with respect to the contractions, whether or not the contractions are perceived as a generalized abdominal tightening, a change in activity or position causes contractions to slow down or stop, the existence of bloody show, status of membranes, e.g. intact or ruptured, a true labor pattern analysis where true labor develops into a regular pattern, with contractions growing closer together, a false labor indicator where the false labor contractions exhibit an irregular pattern, a change in activity discriminator where contractions in true labor continue regardless of activity and even grow stronger with increased activity such as walking, a change in activity indicator for false labor contractions, a location of contraction and or pain indicator and data where in true labor the pain tends to begin high in the female abdomen, radiating throughout the female's entire abdomen and lower back, or visa versa, a location of false labor or pain indicator where in false labor the contractions are often concentrated in the lower abdomen and groin, data and a mode of operation that correlates cervical image data with contraction data, alone or in combination.

The intravaginal device, network, modes of operation are useful to prevent surprises that endanger the health of the mother and or being in the womb, by providing cervical dilation data in realtime or close to realtime. By way of example, a female disregards prelabor symptoms because she believes her due date is several of weeks into the future. When the female goes for a regular check up, the physician may suprising discover that she is partially or fully dilated. In another scenario, a female might leave for the hospital or birthing center with regular contractions that are 3 minutes apart, and after she arrives there, the contractions stop. It is appreciated that the device, network and modes of operation of the device provide realtime data, correlated one to another, that permits the user and or the doctor to have realtime information that guides the instructions to the user whether or not to proceed to the birthing center. False alarms are alleviated, as is the stress and disappointment associated therewith, along with the waste of hospital staff time and resources, as well as the time and nerves of the female and her partner. A method is provided that times entry and admission in a birthing center such that it is "just in time."

Post labor the network and modes of operation provide for a management system for post partum depression through the social network site established during the pregnancy, which may optionally include friends and a support group, during the birth, or post birth. In another variant, one or more nodes on the network include social network functionality, e.g. a link or group on Facebook™, a link to Twitter™, Skye™ or other type of Internet based portal. It is also appreciated that these portals are used in another variant of the invention to communicate data collected by the intravaginal device, and or reports or associated documentation or data, including images to groups on these portals.

In the event an abortion is elected, the device, method and network provide a mode of operation that monitors post abortion events and complications.

During the usage (while on continuously wearing mode) or after usage, depending upon the abovementioned specific circumstances, based upon the permission given by the female user, the intravaginal monitoring device 105 may transmit the captured images/video clips/sensor data to the supporting server 173 (via supporting personal computing devices 171 such as an access point, cell phone or computers). Alternatively, the female user may also opt to watch these images/video clips/sensor data all by herself and decide whether to send them to the support server (and then to the healthcare professionals via the medical support computing systems/devices 175), make her own personal decisions, or discard the images/video clips/sensor data. These options are always available to the individual female user.

Later, the female user may log into her account in the supporting server 173, selectively upload images/video clips/sensor data of interest to her or the healthcare professionals and then give permission to the medical support computing systems/devices 175 of the healthcare professionals for further investigation (of a routine occurrence or a specific condition, for instance). Alternatively, the female user may opt to access suggestions from other users, from another server by sending certain information stored in her account in the supporting server 173 (for no fees at all, for instance). It is appreciated that secure transmission of data is provided to ensure patient confidentiality of the electronic data harvest in one variant. In another variant, it is appreciated that the nodes on the network and the functionality of the device permit two way communication to one or more nodes on the Internet, and ready access to information on the Internet for a user, the partner of the user, and or a medical professional.

Once the healthcare professionals gain access to the images/video clips/sensor data, they are able to provide recommendations/treatments, drug or therapy options via the same supporting server 173 back to the female user or the female users device. In one variant, female users of the network can share treatment or therapy information provided for a condition or event of one user so that a second user can study the treatment or therapy option and or communicate it to her health care professional. These recommendations/treatment options may be informed via emails or directly via the supporting server 173 (which is more secured). These cycles of monitoring and recommendations/treatments can be done routinely during routine checkups, menstrual cycles, menopause, sexually transmitted diseases and pregnancy checkups (may also include pre and/or post coitus periods), thereby saving the time of the female user and the healthcare professionals.

Note that in all cases of the female user, the very same processes are applicable to female animals; in that case instead of female user, the case would be that of a female animal in conjunction with its caretaker and the healthcare professional may be a veterinarian.

Figure 2:
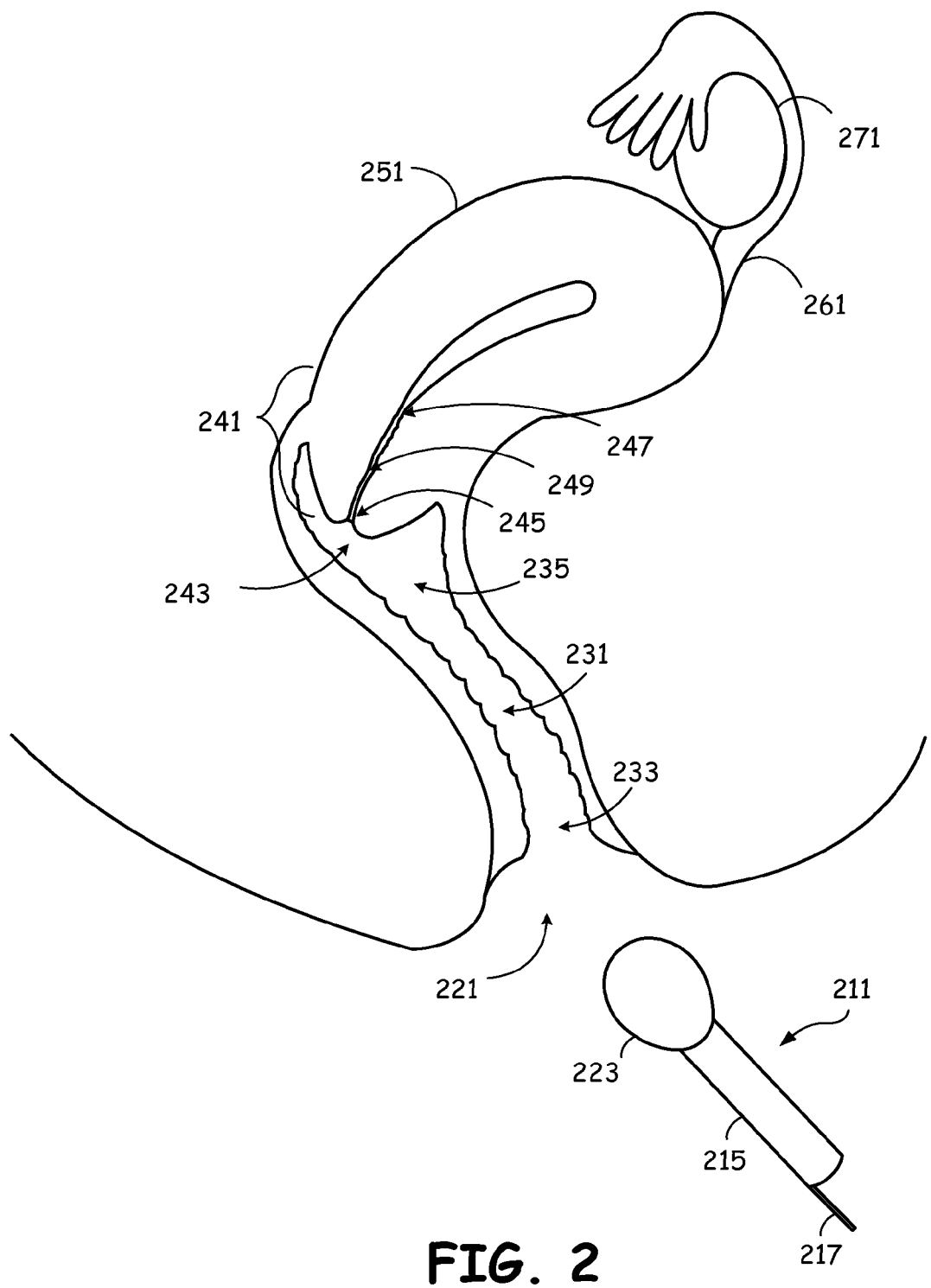
FIG. 2 is a schematic diagram illustrating an intravaginal monitoring device; wherein the device's cap or head, when pushed via vaginal channel to face outer surface of the cervix, takes images of the outer surface of the cervix as well as sensor readings via many of the built-in electronic sensors and sends them out via communication networks for the FIG. 1.

FIG. 2 is a schematic diagram illustrating an intravaginal monitoring device 211; wherein the device's cap or head 223, when pushed via vaginal channel 231 to face outer surface of the cervix 243, takes images of the outer surface of the cervix 243 as well as sensor readings via many of the built-in electronic sensors and sends them out via communication networks for the FIG. 1. Transferring the images/video clips/sensor data from the intravaginal monitoring device 211 to external support servers and for the viewing of the healthcare professionals such as a gynecologist or nurse or obstetrician (or even a veterinarian, in cases of animals) not only saves time while monitoring during routine checkups, menstrual cycles, menopause, sexually transmitted diseases and pregnancy checkups (may also include pre and/or post coitus periods) but also the cost otherwise incurred; which otherwise would necessitate the presence of the female in question at the gynecologist's office, clinic, hospital or facility. Wireless woman's healthcare services are enabled in one variant of the invention, including diagnostic services that can be delivered from lower cost jurisdictions, e.g. where doctor's skill levels are high but salaries are low due to economic conditions and or national healthcare systems. Doctor's are also able to expand their patient and revenue base by servicing more patient's wirelessly over the Internet using the intravaginal device, network, nodes, and modes of operation of the present invention. Moreover, the expertise of physicians is also readily accessed no matter where the physician is located geographically, or where the patient is located geographically.

A visual image typically communicated to healthcare professionals allow the individual female or a gynecologist, obstetrician and or veterinarian to diagnose, offer treatment options, provide realtime management of a labor situation having data readily on hand that would not otherwise be available, and or verify the health conditions. For instance, fluid discharges observed via a moving image video clip (including single image, multiple image, short video clips, medium video clips, or long term video clips), when transferred to a gynecologist's, medical professional's, obstetrician's, or veterinarian's and or technician's computer (or in other variants, mobile phone, smart phone, PDA, or other consumer electronic device), allow the gynecologist or other professional to know the actions to be taken, and to provide instructions to the user as to what actions are to be taken by her or her support network, e.g. partner, family, etc. In this situation, if a labor is ongoing, realtime monitoring may result in an instruction being communicated to a user's device or remote device to stay put because the birth is immenant and there may not be enough time to get to birthing center or other place that can provide assistance. It is appreciated that the invention has particular beneficial impact and can reduce the incidence of births occurring in automobiles, taxis, home (where not desired to be at home) and generally outside the birthing center. Moreover, where a female desires to have a home birth, it is appreciated that the device and network provide a way for realtime data feeds back to the birthing center or medical professional so that in the event of a complication, instructions are sent that are meaningful and also based on realtime harvested data feeds.

Additionally, the illustration also depicts what a gynecologist or other professionals may be interested in learning more information about (by being able to watch the images/video clips/sensor data), that, directly or indirectly, include Vulva 221, Vaginal Channel 231, Exterior Portion of Vaginal Channel 233, Interior Portion of Vaginal Channel 235, Cervix 241, Outer Surface of Cervix 243, Exterior Orifice (opening) of Cervix 245, Interior Orifice 247, Cervical Channel 249, Uterus 251, Fallopian Tube 261, and Ovary 271.

Therefore, using the intravaginal monitoring device 211 and knowledge of reproductive health and well being, the female may herself observe the cervix 241 (and the vaginal discharges thereon or other conditions thereof or therearound) and be able to take many sensor readings (and hence be able to judge health conditions, possibly, in conjunction with a health care and or veterinary professional). And in case of any observable discrepancies, during the course of a female's lifetime, during pregnancy or during normal occurrences of pre and post coitus (due to any worries about STDs) or at all other periods, or upon periodic request by a health care specialist (gynecologist, obstetrician or veterinarian), the images/video clip/sensor data obtained via the intravaginal monitoring device 211 may be utilized in taking precautionary actions. This necessitates communicating, in a secure manner, the images/video clips/sensor data to either regionally or remotely located healthcare professional's computing systems or devices.

To facilitate these, the intravaginal monitoring device 211 may also incorporate and be able to communicate: (a) Camera unit containing wide angle lensing as well as "fish eye" lensing and image recovery; (b) Time stamping all sensor data capture (to be able to follow up and investigate the vaginal conditions by a healthcare professional); (c) Live video used for guidance of the device into place; (d) Linear, symmetric device with a very flexible neck and stem to assist in fitting the space; and (e) Making the intravaginal monitoring device able to bend and face toward cervix (straight ahead, in a line of sight; note that the female person may partly have to work the intravaginal monitoring device 211 to make it orient properly,—this can also be accomplished by viewing the images in an external device).

Figure 3:
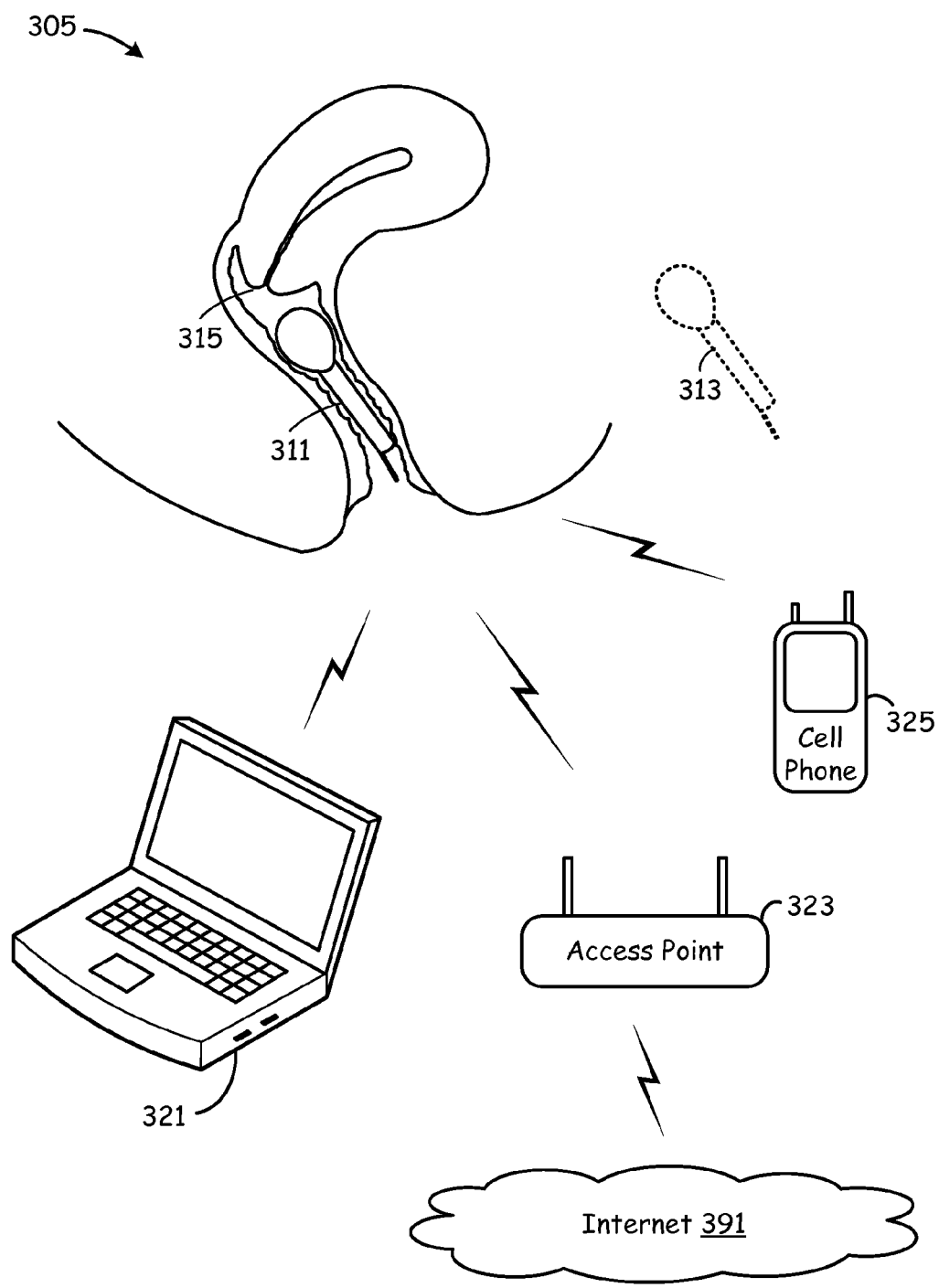
FIG. 3 is a schematic block diagram illustrating the supporting network infrastructure for the intravaginal monitoring device of the FIG. 1; wherein the intravaginal monitoring device captures images and sensor readings, and communicates to immediate external electronic devices as well as receives control signals via the immediate external electronic devices.

FIG. 3 is a schematic block diagram illustrating the supporting network infrastructure for the intravaginal monitoring device 311, 313 of the FIG. 1; wherein the intravaginal monitoring device 311, 313 captures images and sensor readings, and communicates to immediate external electronic devices 321, 323, 325 as well as receives control signals via the immediate external electronic devices 321, 323, 325.

The intravaginal monitoring device 311, 313 may be in place in the vaginal channel, fully to be concealed or partially to be partially visible from the outside of the vagina (such as 311) or may be placed in a close by locality (such as 313) of the external electronic devices 321, 323, 325 (alternatively, supporting personal computing devices 321, 323, 325) after the usage; either way, the intravaginal monitoring device 311, 313 is able to communicate with the supporting personal computing devices 321, 323, 325, as per the firmware instructions or downloadable instructions. These instructions or program codes of usage of the intravaginal monitoring device 311, 313 are tailored to specific circumstances of the female such as routine checkups, menstrual cycles, menopause, sexually transmitted diseases and pregnancy checkups. The processes of healthcare checkups and treatments may begin by the female user following these instructions, in conjunction with a healthcare professional's recommendations. Once the process of checkup and treatment is initiated, all that the female user needs to do is to follow the written or oral instructions available in the supporting server's web pages (which are accessible via the computer 321, access point 323 and Internet 391, for instance).

For instance, in case of a computer 321 or cell phone 325, the communication between the intravaginal monitoring device 311, 313 and the computer 321 or cell phone 325 may occur by ways of Bluetooth, infrared or WiFi communication technologies; or, simply via a USB connection, in another variant a Wimax communications standard is used and one way or two data communication and instruction communication feeds go to other nodes of the network. In one variant, the device automatically detects the existence of an Internet connection and connects thereto. In another variant, the device has continuous access or activated access to a mobile phone communication network using mobile phone communications technology. Once the images/video clips/sensor data are communicated from the intravaginal monitoring device 311, 323 to the supporting personal computing devices 321, 323, 325; they can be utilized in one or more ways of: (a) Watching the images/video clips/sensor data in the supporting personal computing devices 321, 323, 325 by oneself and taking any precautionary actions (such as in case of immediately after conception); (b) Transfer the images/video clips/sensor data from the supporting personal computing devices 321, 323, 325 to a supporting server; (c) Give permission to an external healthcare professional to observe and recommend treatments; (d) Send the images/video clips/sensor data to another website requesting for assistance regarding a particular condition; (e) Maintain time stamped images/video clips/sensor data and utilize them in research and developments, by a third party healthcare related professionals, processing of the data to diagnose conditions and or infections, processing of the data to suggest treatment options, processing of the data using statistical data manipulation software, processing some or all of the data with an interface to billing and invoicing software, processing some or all of the data or related data with an interface to reimbursement software, processing of the data with an interface to billing and reimbursement codes, and or (processing of the data to make predictions), alone or in combination. Many more alternative usages are also contemplated and further discussed in the descriptions for the succeeding FIGs.

Figure 4:
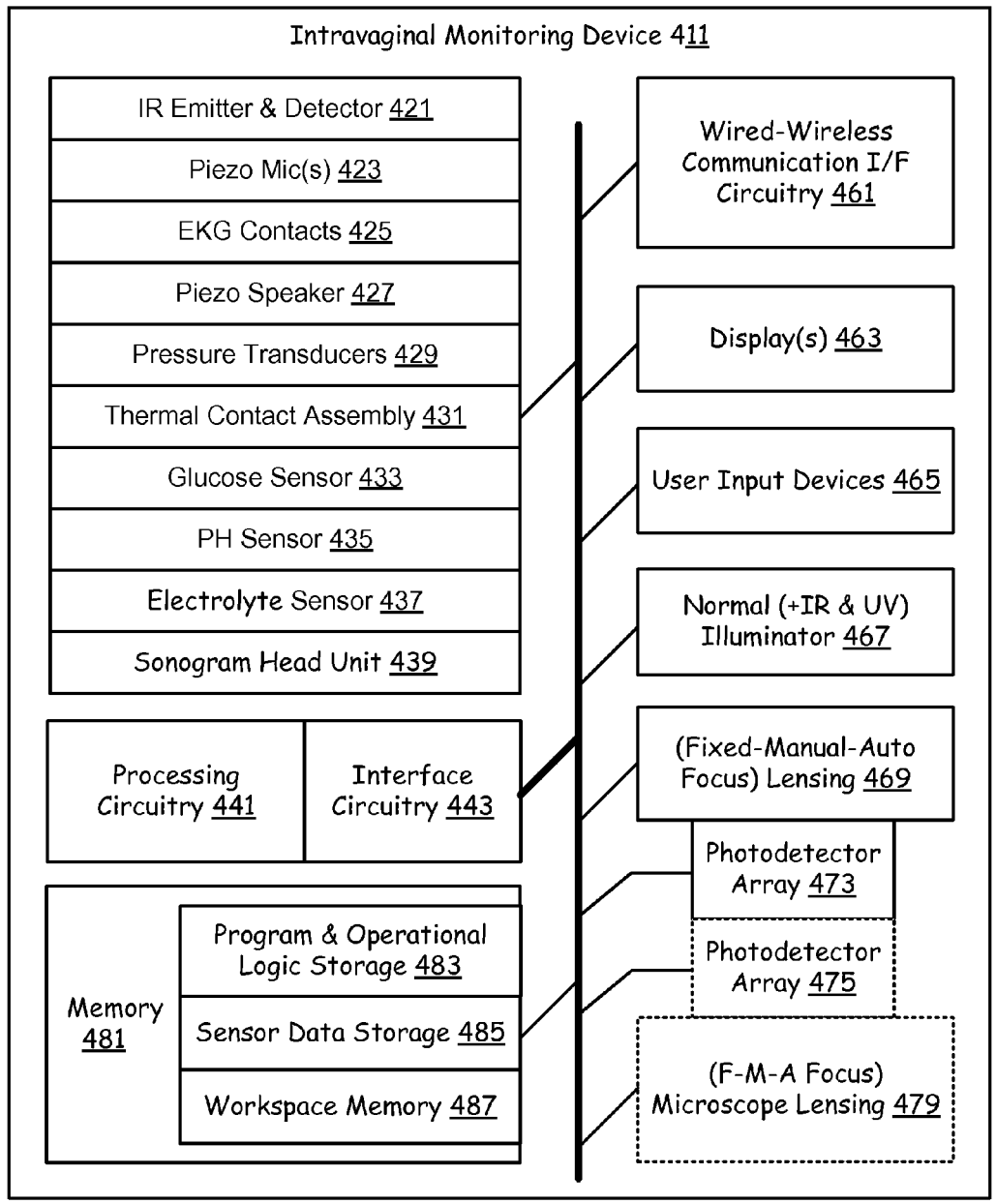
FIG. 4 is a schematic block diagram illustrating the intravaginal monitoring device of the FIG. 3; wherein the intravaginal monitoring device contains wired and/or wireless communication interfaces as well as firmware and program & operational logic codes that makes it possible for the intravaginal monitoring device to communicate with the immediate external electronic devices as well as receive control signals via immediate external electronic devices.

FIG. 4 is a schematic block diagram illustrating the intravaginal monitoring device 411 of the FIG. 3; wherein the intravaginal monitoring device 411 contains wired and/or wireless communication interfaces 461 as well as firmware and program & operational logic codes 483 that makes it possible for the intravaginal monitoring device 411 to communicate with the immediate external electronic devices (alternatively, supporting personal computing devices 321, 323, 325 of the FIG. 3) as well as receive control signals via immediate external electronic devices.

In specific, the firmware and program & operational logic codes 483 allow the intravaginal monitoring device 411 to perform in accordance with specific logic, in one variant, that includes: (a) Receiving and/or executing instructions, in case of wearable intravaginal monitoring device 411, as to when to switch on and off, when to take images/video clips/sensor data, and at what interval they should be taken; (b) Receiving and/or executing instructions to vibrate/beep, and then, switch off and transfer data to an external device or external servers (such as after enough data to make diagnosis has been taken and it is time to switch off until some other time or in emergency situations such as sometime before delivery of a baby); (c) Receiving and/or executing instructions that involves exceeding limits in cases of sensor data; and/or (d) Monitoring the battery operations and informing the user to recharge batteries, if need be; and so forth.

In anther variant, the device is worn by the user continuously, but its functionality is turned on or off, and or modes of operation of the device are activated or deactivated, or sensing capabilities are activated or deactivated, periods and or periodicity of data capture are modulated, remotely from another node on the network by a healthcare professional or other user.

The sensors and devices that are incorporated into the intravaginal monitoring device 411 may include components of one or more of: (a) IR emitter and detectors 421, to monitor temperature; (b) Piezo microphones 423, to monitor heartbeat sounds of fetus, for instance; (c) EKG Contacts 425, to take electrocardiogram graphs of heartbeat of a fetus, for instance; (d) Piezo speaker 427, to produce a soothing sound for the fetus, for instance; (e) Pressure transducers 429, to make pressure measurements within the intravaginal channel, to monitor dilations, for instance; (f) Thermal contact assembly 431, to take temperature measurements in cases of wearable intravaginal monitoring device 411, for instance; (g) Glucose sensor 433, to take glucose measurements; (h) PH sensor 435; (i) Electrolyte sensor 437; (j) brain activity monitors, and/or (k) Sonogram head unit 439.

In all of the above-mentioned sensor cases, a processing circuitry 441 executes, as mentioned above, the operational logics, and takes measurements at appropriate intervals and also verifies if the limits are exceeded and precautionary actions should be taken. Other components of the intravaginal monitoring device 411 depicted include displays 463, user interface devices 465, normal (infrared and ultraviolet) illuminators 467, fixed-manual-auto focus lensing 469, bunch of photodetector arrays 463, 475 and fixed-manual-auto focus microscopic lensing 469, lens zoom capability (mechanical and or digital).

Figure 5:
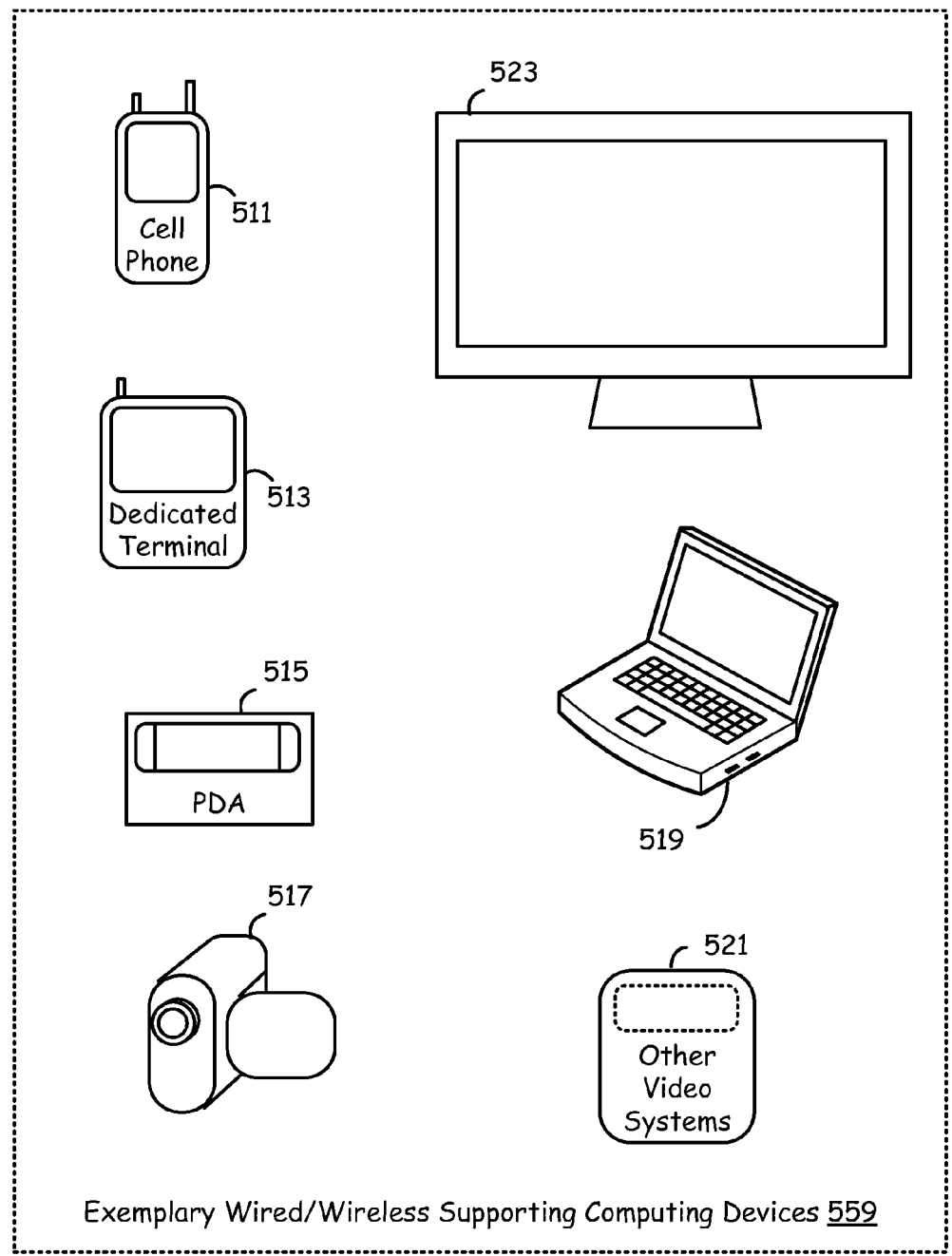
FIG. 5 is a schematic diagram illustrating exemplary wired and/or wireless computing devices that support the intravaginal monitoring device of the FIG. 3.

FIG. 5 is a schematic diagram illustrating exemplary wired and/or wireless computing devices 559 that support the intravaginal monitoring device of the FIG. 3. The intravaginal monitoring device is capable of communicating with many variety of supporting personal computing devices 511, 513, 515, 517, 519, 521, 523, either via a USB connection, any other wired connection or Bluetooth, infrared, WiFi wireless connections, medical data transmission wireless standards, WiMax and the like.

Among these supporting personal computing devices include, but not limited to: (a) Digital photo and video devices; (b) Car tech and GPS devices; (c) Cell phones and smartphones; (d) Computers and hardware, e.g. netbooks, so forth; (e) Gaming devices; (f) Home theatre devices; (g) MP3 and video players; (h) Televisions; and/or (i) other consumer electronic devices. The depiction shows some of these more popular devices of today, they include: cell phone 511, dedicated terminal 513, PDA (Personal Digital Assistant) 515, video camera 517, computers 519, televisions 523 and other video systems 521. A dedicated terminal may merely include a display unit with basic communication capabilities such as wired USB connection or Bluetooth connection capabilities.

Figure 6:
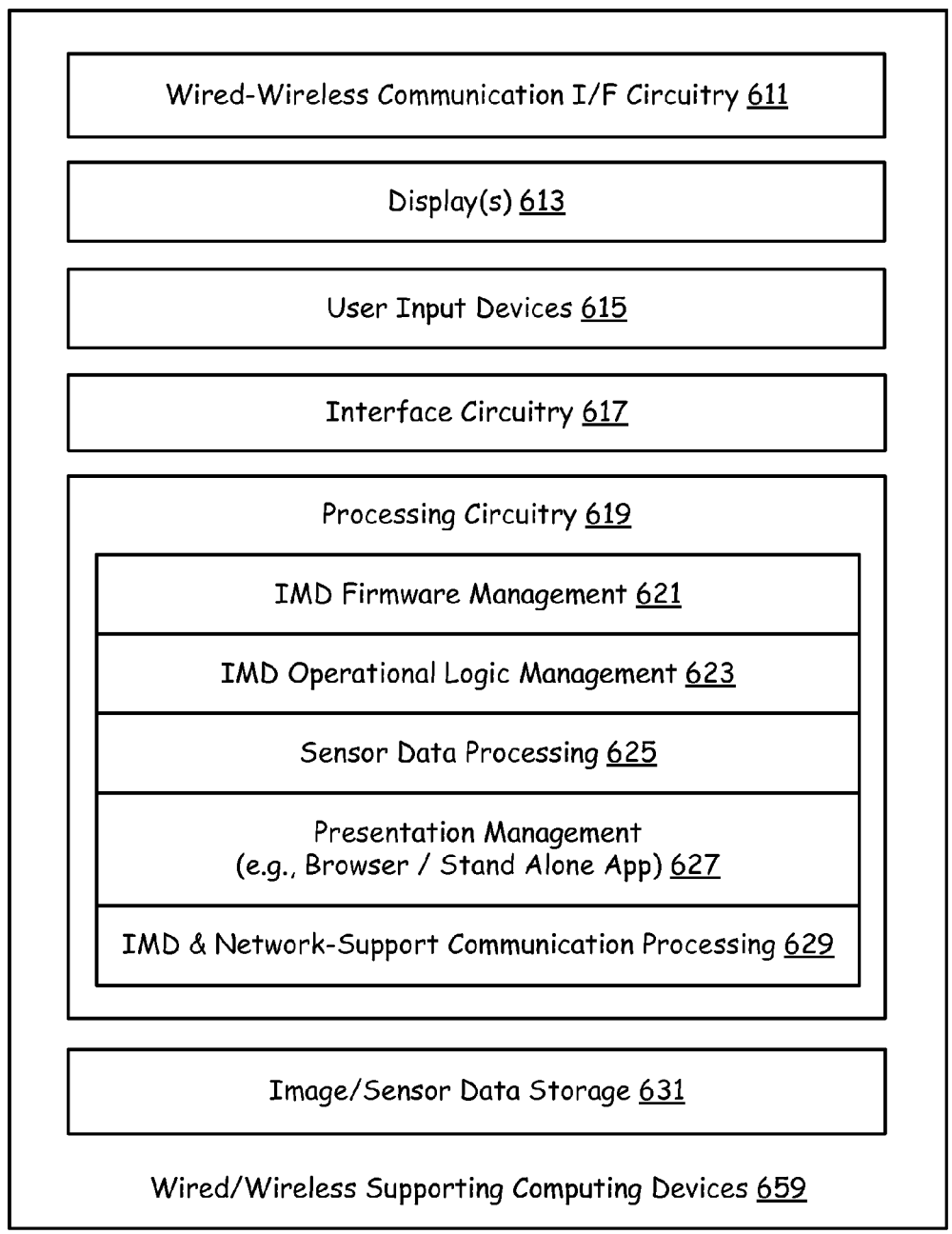
FIG. 6 is a schematic block diagram illustrating the wired and/or wireless computing devices of the FIG. 5 that support the intravaginal monitoring device.

FIG. 6 is a schematic block diagram illustrating the wired and/or wireless computing devices 659 of the FIG. 5 that support the intravaginal monitoring device. In specific, to enable communications of control signals and image/video clip/sensor data, the wired and/or wireless computing devices 659 contain many blocks that include wired-wireless communication circuitry 611, display 613, interface circuitry 617 and image/video clip/sensor data storage 631. The image/video clip/sensor data storage 631 may have limited space to contain many of the data transferred from the intravaginal monitoring device; nonetheless, the image/video clip/sensor data may be transferred to an external support server for secured storing.

The processing circuitry 619 itself contains many blocks (that may include downloaded firmware/software that makes the corresponding functionalities possible), that include: (a) Intravaginal monitoring device firmware 421; (b) Intravaginal monitoring device operational logic management; (c) Sensor data processing 425; (d) Presentation management (for instance, browser/stand alone applications); and/or (e) Intravaginal monitoring device and network support communications processing 429 (here, for instance, the user may be able to selectively upload few of the image/video clip/sensor data).

Figure 7:
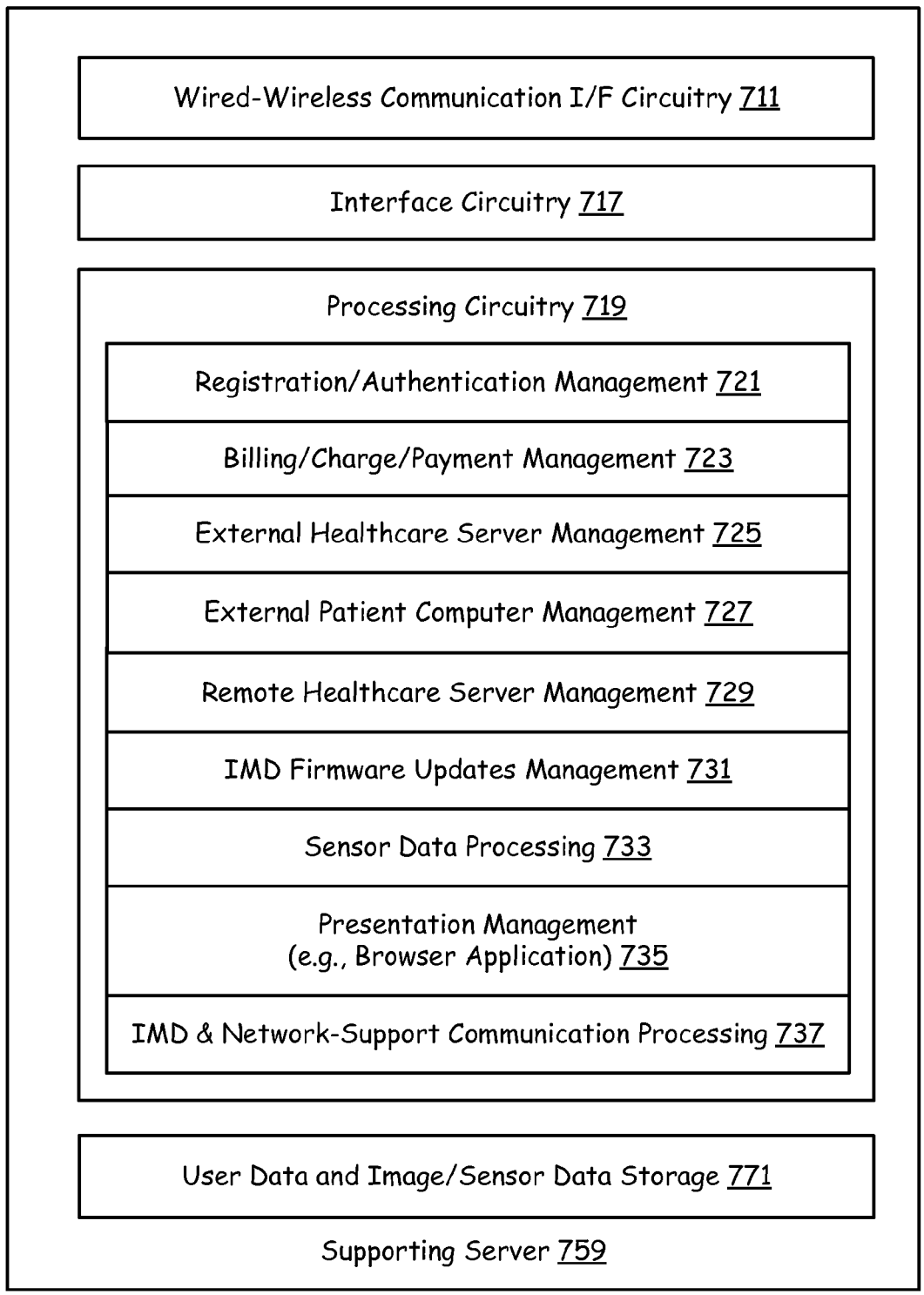
FIG. 7 is a schematic block diagram illustrating a supporting server of the FIG. 1 that supports the intravaginal monitoring device.

FIG. 7 is a schematic block diagram illustrating a supporting server 759 of the FIG. 1 that supports the intravaginal monitoring device. Although in some embodiments, the supporting server may be bypassed and the intravaginal monitoring device may directly interact with supporting personal computing devices or medical support computing system/devices; in most other embodiments, the supporting server 759 acts as a central management hub and maintains user (patient) accounts, healthcare professional accounts (via browser applications, for instance). The supporting server 759 also makes it possible for communications between users and healthcare professionals to occur routinely and systematically, and provides software and firmware supports to the users and healthcare professionals.

In addition, the supporting server 759, in some cases, takes hold of the intravaginal monitoring device entirely and sends live images/video clips/sensor data to the healthcare professionals, upon permission from the user and as per the directions from the healthcare professionals (such as when live observations and inspections need to be done). In addition, the supporting server 759 also allows the users to share images/video clips/sensor data via a social networking system (that permits the users, in conjunction with the intravaginal monitoring devices and/or wired/wireless supporting computing devices, to share their experiences). For instance, the users may wish to share information about their individual conditions, treatment options, their experiences with various doctors, contact information, so forth; and in return may get some advice or tips from others. Moreover, the supporting server 759 also makes it possible to bill and charge the users and make payments to the healthcare professionals for their services.

To make the abovementioned management (and sharing of experiences) possible, the supporting server 759 contains many modules, including wired/wireless communication interfaces circuitry 711, (user) interface circuitry 717, processing circuitry 719, user data and image/sensor data storage 771. The processing circuitry 719, in turn contains modules of registration/authentication management 721, billing/charge/payment management 723, external healthcare server (or, medical support computing systems/devices) management 725, external patient computer (or, supporting personal computing devices) management 727, remote healthcare server management 729, intravaginal monitoring device firmware updates management 731, sensor data processing 733 and intravaginal monitoring device and network support communication processing 737.

Figure 8:
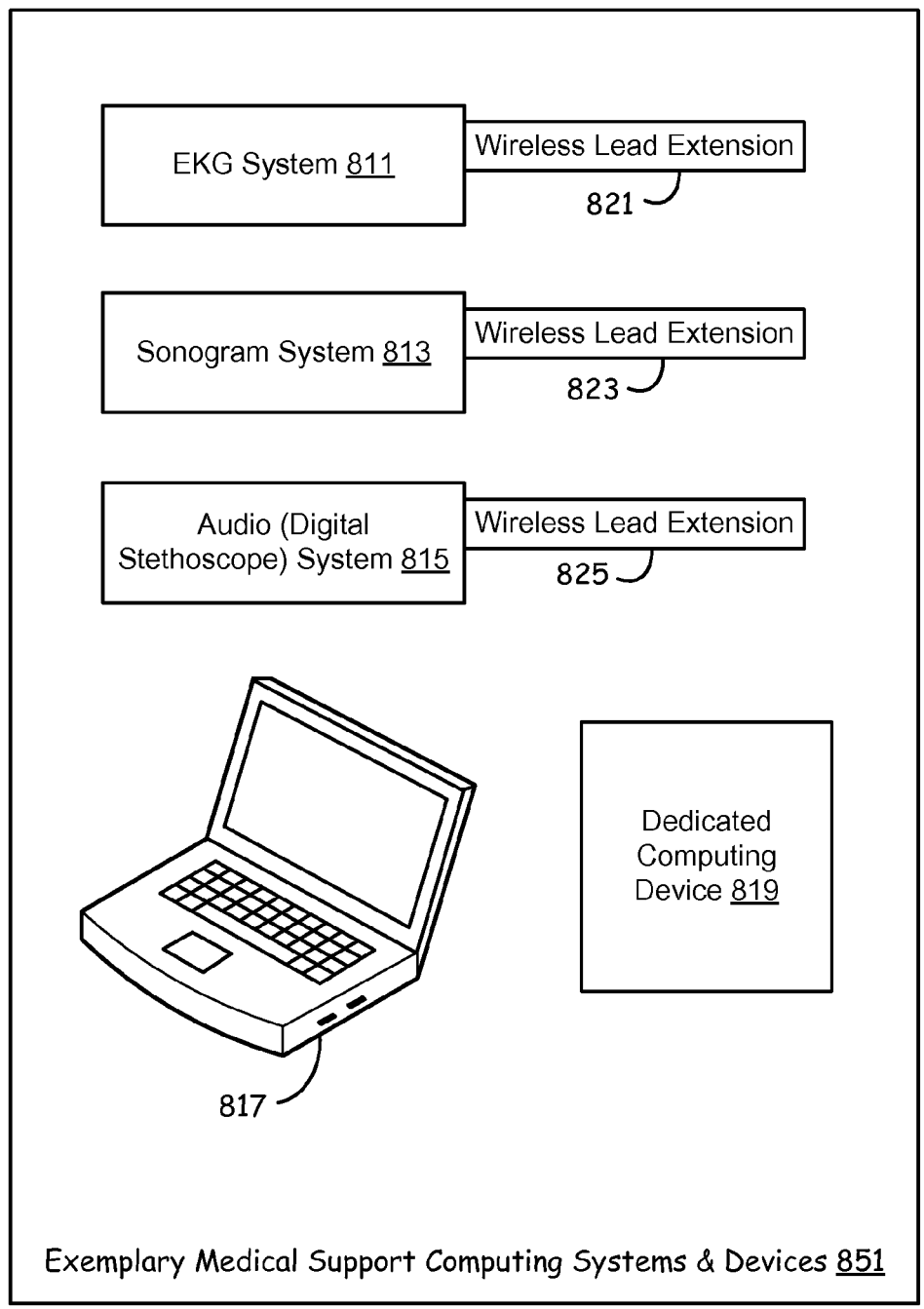
FIG. 8 is a schematic diagram illustrating exemplary medical support computing systems and devices of the FIG. 1 that support an intravaginal monitoring device.

FIG. 8 is a schematic diagram illustrating exemplary medical support computing systems and devices 851 of the FIG. 1 that support an intravaginal monitoring device. The devices/equipments that may be incorporated within the intravaginal monitoring devices may include electrocardiogram (ECG or EKG) system 811, sonogram system 813, audio (digital stethoscope) system 815, wirelessly enabled sunglass, billing and invoicing systems, and or reimbursement systems, alone or in combination.

These devices or equipments 811, 813, 815 may be of a low powered variety, and only the sensor portion of them may be incorporated within the intravaginal monitoring device. The rest of the processing may occur outside of the intravaginal monitoring device, possibly in a dedicated computing device 819 (or, medical support computing systems/devices 819), external patient's computer 817 (or, supporting personal computing devices 817) or even by the supporting servers. To make the further processing of the information obtained by the sensors of these equipments possible, external wireless lead extensions 821, 823, 825 exist within the intravaginal monitoring devices.

Figure 9:
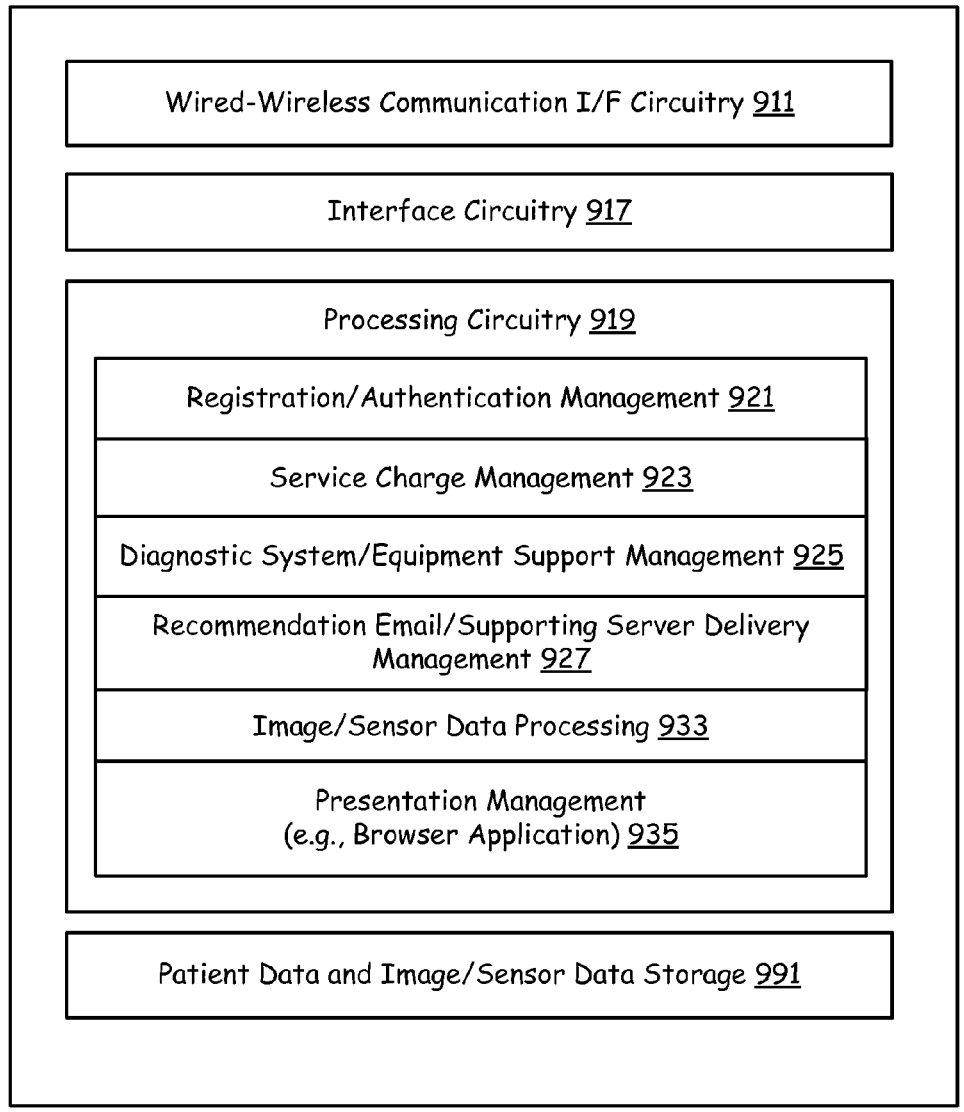
FIG. 9 is a schematic block diagram illustrating the medical support computing systems and devices of the FIG. 8 that support the intravaginal monitoring device.

FIG. 9 is a schematic block diagram illustrating the medical support computing system and device 959 of the FIG. 8 that supports the intravaginal monitoring device. The intravaginal monitoring device, having a variety of equipments, either via supporting personal computing devices and supporting servers or directly, is capable of feeding images/video clips/sensor data to the medical support computing system and device 959 for further processing. Some levels of preprocessing may occur in the intravaginal monitoring device or in conjunction with supporting personal computing devices and supporting servers; nonetheless, the healthcare professionals may finally determine how the information should be processed, for them to be able to make proper diagnosis of a condition, for instance. In addition, the healthcare professionals, once diagnosis is done, are able to provide recommendations and treatments.

To make the abovementioned diagnosis, recommendations/treatments possible (by the healthcare professionals), the medical support computing systems/devices 959 contains many modules, including wired/wireless communication interfaces circuitry 911, (healthcare professional) interface circuitry 917, processing circuitry 919, patient data and image/sensor data storage 991. The processing circuitry 919, in turn contains modules of registration/authentication management 921, service charges (payment) management 923, diagnostic system/equipment support management 925, recommendation email/supporting server delivery management 927, image/sensor data processing 933 and presentation management (for instance, browser application) 935.

In addition, the diagnostic system/equipment support management 925 also allows the medical support computing systems/devices 959 to communicate data between other medical systems/devices (for instance, expectant mother's devices communicating data between each other or between pluralities of devices used in a maternity hospital, and or other electronic devices that are placed on the exterior of the woman, and that optionally provide vital function monitoring of the being in womb and or expectant mother, and that wirelessly communicate with the intravaginal device or another remote device. By way of example, the network includes the intravaginal device and an external electronic, self powered patch including sensors and or a camera assembly. The birth proceeds and the woman is fully dilated at 10 cm of cervical dilation, or earlier. The intravaginal device is removed from the birth canal. The electronic patch (which includes one or more devices) wireless feed continued data to an external unit regarding the being in womb's and or pregnant mother's heart rate and other vital functions. In one variant, the external patch and intravaginal device share and communicate data therebetween. This feature enables the midwife, doctor or other medical professional to have a continuous stream of clinically relevant data, e.g. if the being in womb is being stressed as a result of the birthing process, the position of the being in the womb, etc. This data is also used to decide if there is a need to proceed with a Caeserean section procedure or whether a natural vaginal birth can be concluded.

Figure 10:
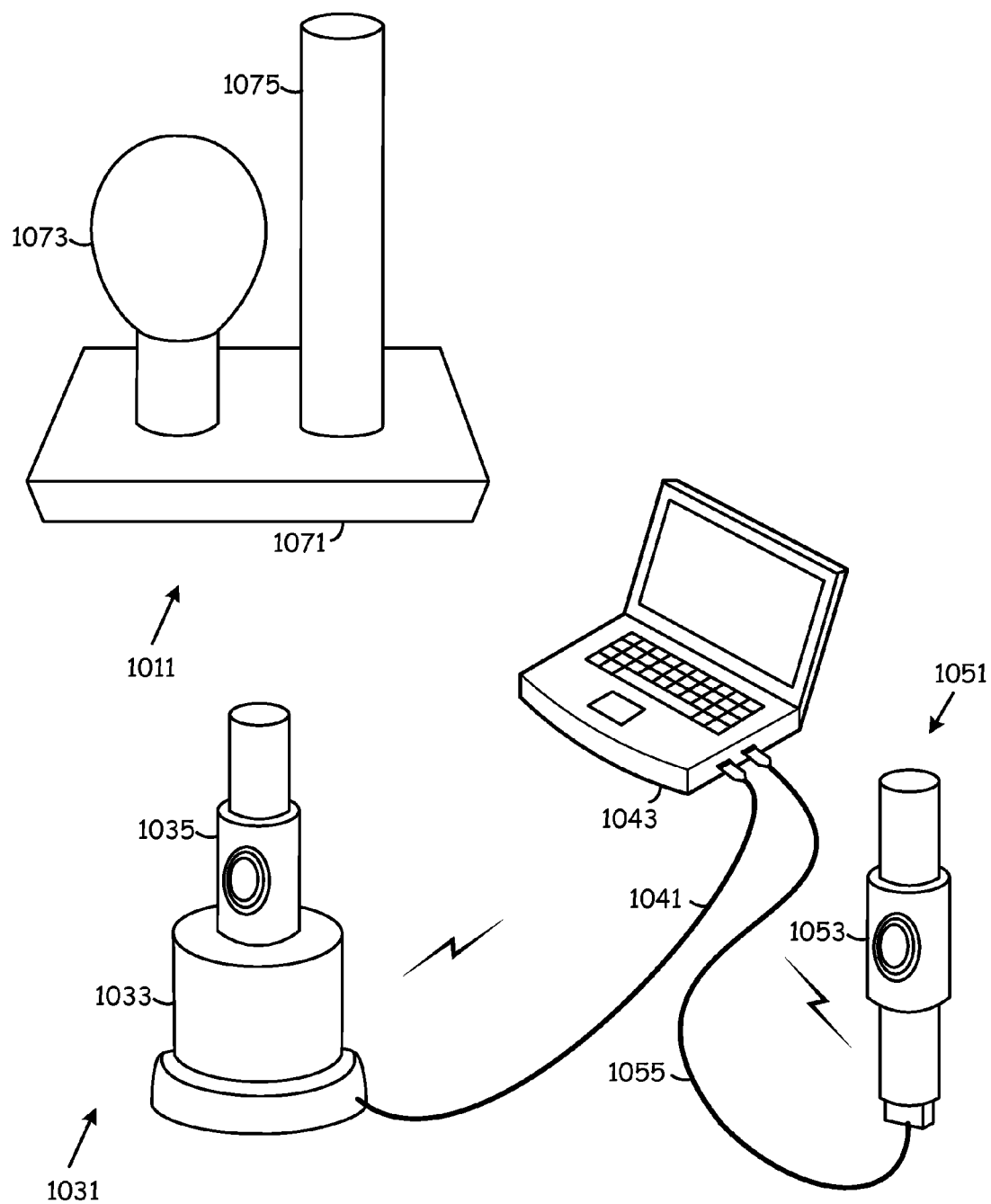
FIG. 10 is a schematic diagram illustrating the docking systems for the intravaginal monitoring device of the FIG. 1 that assist in communicating with the external supporting network infrastructure.

FIG. 10 is a schematic diagram illustrating the docking systems for the intravaginal monitoring device of the FIG. 1 that assist in communicating with the external supporting network infrastructure. The intravaginal monitoring device has three parts: the bulb or cap 1073, stem 1035, 1053 and a base 1075 unit. When they are assembled together, they make up one complete intravaginal monitoring device.

To make communications between the intravaginal monitoring device and supporting personal computing devices 1043, supporting servers, and medical support computing systems and devices possible, in some of the embodiments, a docking system 1031 is used. The docking system 1031 (consisting a base unit 1033) has built-in wired and wireless communication circuitry that allows via USB cables or wirelessly communicate with the computer, when the stem 1035 (that contains all of the stored images/video clips/sensor data) is docked. Nonetheless, direct communication between the stem 1053, as depicted, via USB cables 1055 or wirelessly, with the computer, is also possible in many other embodiments. During those times when the bulb or cap 1073 and base 1075 unit are not in use, another docking unit 1071 is also provided, to keep those parts safe.

Figure 11:
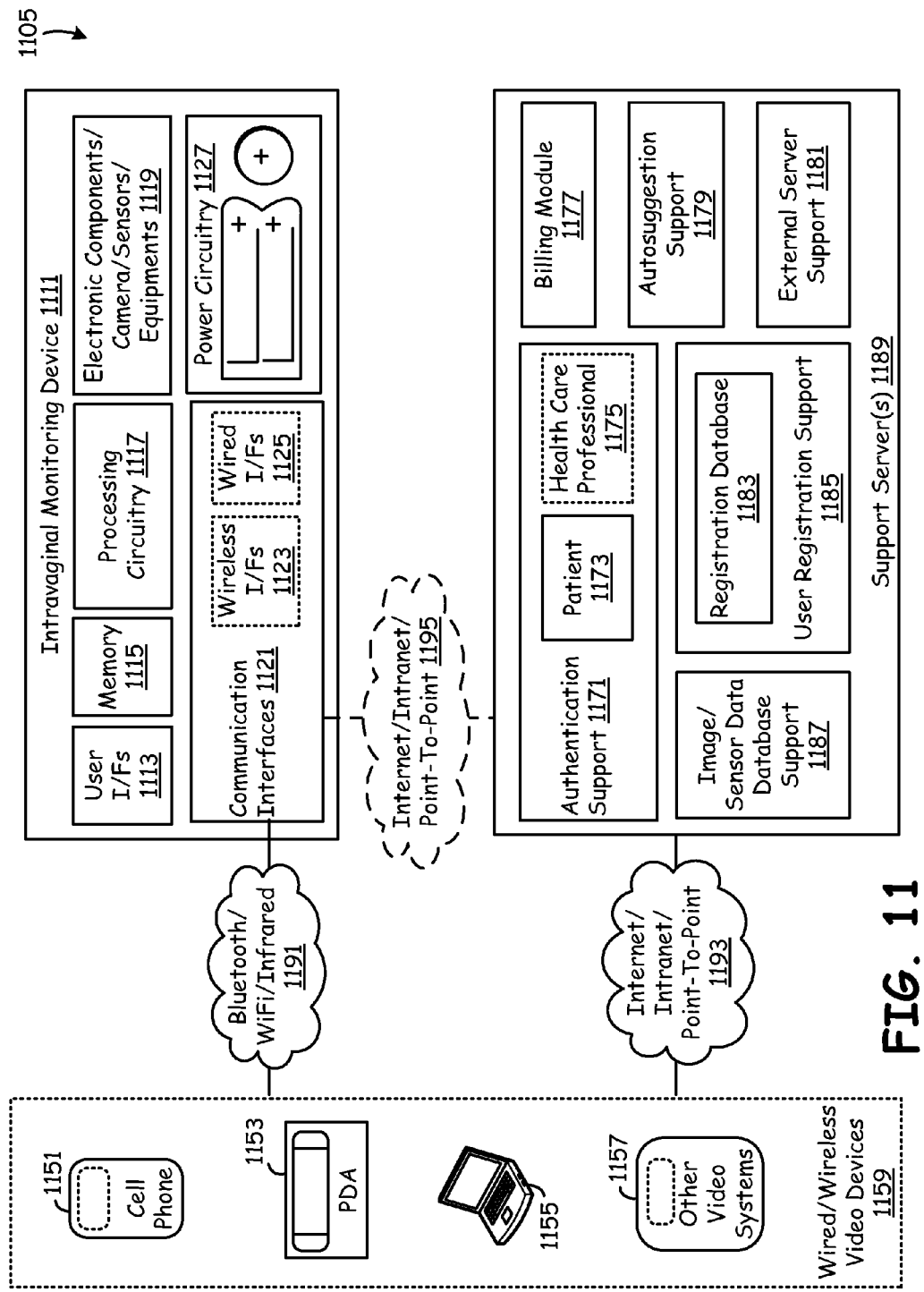
FIG. 11 is a schematic block diagram illustrating a supporting network infrastructure for an intravaginal monitoring device; wherein the intravaginal monitoring device communicates via a communication interface to external devices and/or external servers via wired/wireless, point-to-point, Internet/Intranet network pathways.

FIG. 11 is a schematic block diagram illustrating a supporting network infrastructure for an intravaginal monitoring device 1111; wherein the intravaginal monitoring device 1111 communicates via a communication interface 1121 to external devices 1159 and/or external servers 1189 via wired/wireless, point-to-point, Internet/Intranet network pathways 1191, 1193, 1195. In specific, the illustration depicts electronic components within the hermetically sealed intravaginal monitoring device 1111 and within the electronic infrastructural supporting devices 1159, 1189 external to the intravaginal monitoring device 1111, that includes electronic video systems 1159, external servers 1189, consumer products such as an iPod (tm), iPhone™, etc. and diagnostic equipments in healthcare centers (further described with reference to the FIG. 12).

The electronic components located within the hermetically sealed intravaginal monitoring device 1111 include camera/sensors/equipments 1119 (that may include sonogram and electrocardiogram), communication interfaces 1121, user interfaces 1113, memory 1115, processing circuitry 1117 and power regulator and management circuitry 1127.

The communication interfaces 1121 include wireless 1123 (such as Bluetooth, WiFi, Infrared) and wired 1125 interfaces that allow the captured and temporarily stored images and sensor data in the memory 1115 to be transferred to external wired/wireless video devices 1159, such as cell phones 1151, personal digital assistant 1153, computers 1155 and other video systems 1157. The other video systems 1157 may include digital photo and video devices, car tech and GPS devices, cell phones and smartphones, computers and hardware (e.g., notebooks, etc.), gaming devices, home theater devices, MP3 and video players and televisions. In yet a further aspect of the invention, the device includes global positioning system electronics. The global positioning electronics are used to identify the location of a device, a first device in relation to other devices, e.g. mobile phones of a husband or a doctor, and in relation to the location of hospitals, birthing centers, and to time determine the distance and time of travel and arrival, and location of, e.g. an expectant mother to a hospital, an obstetrician to a hospital for a birth, a father to the birth of his child.

The captured and temporarily stored images and sensor data from these wired and/or wireless devices 1159 may be observed by the female or a healthcare professional or may later be transferred to external servers 1189. Finally the female may utilize them whichever the way she deem fit, that includes sharing them (and requesting for more information via Internet regarding a particular condition) or transferring them to healthcare centers. Alternatively, the captured and temporarily stored images and sensor data in the memory 1115 may also be transferred (via, wireless or wired communication paths) directly from the intravaginal monitoring device 1111 to the external servers 1189.

To enable all of the abovementioned possibilities, the support servers 1189 contain modules of authentication support 1171 (in turn including patient 1173 and healthcare professional 1175 authentications), user registration support 1185 (in turn including registration database 1183), image/sensor data database support 1187, billing module 1177, autosuggestion module 1179 and external server support 1181. The autosuggestion module 1179 and external server support 1181 makes it possible for the user to get advices and suggestions from other interlinked websites, based upon the diagnosis and condition.

Figure 12:
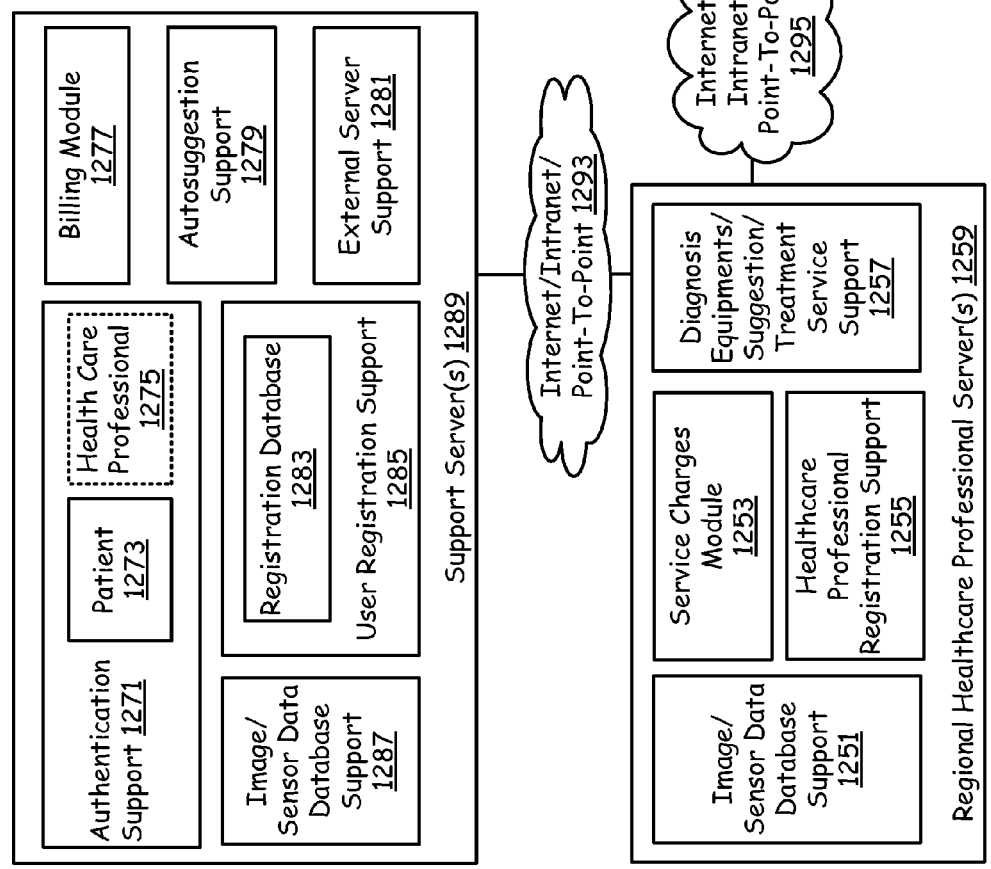
FIG. 12 is a schematic block diagram illustrating supporting network infrastructure for an intravaginal monitoring device that is, in addition to the external devices and/or external servers of the FIG. 11, also supported by regional and remote healthcare professional servers, via wired/wireless, point-to-point, Internet/Intranet network pathways.

FIG. 12 is a schematic block diagram illustrating supporting network infrastructure for an intravaginal monitoring device that is, in addition to the external devices and/or external servers 1289 of the FIG. 11, also supported by regional and remote healthcare professional servers 1259, 1239, via wired/wireless, point-to-point, Internet/Intranet network pathways 1293, 1295. The support server 1289, in conjunction with the regional and remote healthcare professional servers 1259, 1239, enables many of the below mentioned functionalities.

The device and the nodes on the network described include functionality or modules to process and correlated intravaginal and extravaginal physiologic or personal use information with advertising related information such as cost per click (CPC) or cost per thousand impressions. Two primary models for determining cost per click: flat-rate and bid-based are used by way of example in the invention contained herein. In both cases the advertiser (e.g. a woman's consumer product marketer, a baby food vendor, a diaper's vendor), considers the potential value of a click from a given source. This value is based on the type of individual the advertiser is expecting to receive as a visitor to his or her website, (who's advertising is made directly on a remote device itself or intravaginal device) and what the advertiser can gain from that visit, e.g. revenue, product visibility. By way of example, an advertisement for baby diapers appears on a smart phone or computer of an expectant mother or expectant father, this information is presented simultaneously with physiological (or other information from the device) on the smart phone or computer in a separate window. In another variant, the advertising information is presented for a time out period and charged to the advertiser based upon the amount of time that the advertisement window appears on the target's remote device. The device itself communicates with one or more nodes on the network to communicate the time the advertisement appeared on the expectant mother or father's smart phone or computer. Based upon the viewing time, or cost per click or cost per thousand impressions, the advertiser then gets billed for the advertising using a billing module based on one or more nodes of the network.

In another variant of the invention, the flat-rate model module is used. A fixed charge is entered on one or more computers connected to nodes of the module that establish what will be paid for each click. This information, in one variant of the invention take from rate card database that lists the CPC within different areas of a website presenting data from the intervaginal device. These various amounts are often related to the content on pages displayed.

In another variant of the invention, the bid-based model module is used on one or more nodes of the network to which data from the intravaginal device is communication. By way of example, the a software module is used to permit a first advertiser to compete against other advertisers in a private auction hosted by a website associated with the intravaginal device data or data collected from a plurality of intravaginal devices or, more commonly, an Internet based advertising network. Data on the network for each advertiser informs the host of the maximum amount that the advertiser is willing to pay for a given ad spot. The auction plays out in an automated fashion every time a visitor triggers the ad spot on the network to which the intravaginal device is communicatively linked.

In another variant of the invention, the major advertising networks are connected to the network of a plurality of intravaginal devices are communicatively linked. Contextual ad data is placed on the web properties of a 3rd-party to which the intravaginal devices are communicatively linked. Publishers electronically sign up to host ads on behalf of the network. In return, they receive a portion of the ad revenue that the network generates, which can be anywhere from 50% to over 80% of the gross revenue paid by advertisers. These properties arc often referred to as a content network and the ads on them as contextual ads. Advertisers are automatically and electronically billed and pay for each click they receive, with the actual amount paid based on the amount bid. It is common practice amongst auction hosts to charge a winning bidder just slightly more (e.g. one euro cent) than the next highest bidder or the actual amount bid, whichever is lower To maximize success and achieve scale, automated bid management systems are deployed on the intravaginal device network of the present invention and include method steps to implement automated bid management and advertising systems on one or more nodes on the intravaginal device network. These systems can be used directly by the advertiser, though they are more commonly used by advertising agency computer systems that offer PPC bid management modules as a service. These tools generally allow for computerized and automated bid management at scale, with thousands or even millions of PPC bids controlled by a highly automated system. The system generally sets each bid based on the goal that has been set for it, such as maximize profit, maximize traffic at breakeven, and so forth. The system is usually tied into the advertiser's website and fed the results of each click, which then allows it to set bids.

By way of further example, a targeted advertising module is used in the present invention. Intravaginal device detects a female condition, e.g. a pregnancy, a sexually transmitted disease (STD), a precancerous condition, a cancer, a medical abnormality. This information is communicated to one or more nodes on the network. Advertising data for the treatment of the STD, e.g. for a drug used to treat the STD or other condition, from a particular pharmaceutical company or one or more companies, is then sent to the intravaginal device or other remote device on the network, for a user or doctor to review. Treatment option data are also communicated in another variant of the invention to the intravaginal device and or remote device. With respect to pregnancy data, baby gift data or products used with babies are displayed on the intravaginal device or remote device. In yet another aspect of the information, a module is provided to mask, conceal or render anonymous the identity of a user of the intravaginal device while still permitting the information concerning the treatment for the users condition, state or intravaginal event to be used to direct advertising to the user needing a particular drug or treatment regimen.

In yet a further aspect of the invention (optionally using GPS functionality for locating or placing the intravaginal device at a geographic location, e.g. or a remote device, (e.g. mobile phone communicating the intravaginal device), patient candidate and drug recipient candidates data is collected. User specific condition or event data is collected on one or more nodes on the network and correlated to treatment advertising data, and or medical specialist, or hospital data. It is appreciated that drug companies will be able to provide targeted advertising data or their therapies and/or drugs to exactly the users who are suffering from conditions or events which their products provide beneficial treatments, e.g. drugs that treat STD's, drugs that treat cancers, etc.

In yet other aspects of the invention a user profile module is provided, and a method of monitoring and controlling the spread of sexually transmitted diseases. The user enters personal information, medical information, condition information, social information, e.g. the names of sex partner data, date and times of intercourse with specific partners, etc. This information is correlated with data collected from the intravaginal device. By way of further example, a sexually active female takes baseline data with the intravaginal device of the present invention. The data is time and date stamped, a record of the health or condition of her cervix is recorded on the device or one or more nodes of the network. She then has intercourse with a sex partner. In one scenario, if the partner is free of STDs a follow up record of the cervical or vaginal condition can be compared with the baseline data and archivally recorded. In another scenario, if the sex partner had an STD, then the user uses the device and notices that there are abnormal cervical and or vaginal changes, and these are archivally recorded and or an alert is sent to a remote device, e.g. the user's or doctor's, and one or more of the advertising modules above is activated. Similarly, the sex partner is notified early of the STD condition. It is appreciated that the early notification of the condition for the user and the sex partner can stop the spread of the disease to other sex partners that may occur, e.g. in the case of HPV transmission.

To make the abovementioned functionalities possible, the support servers 1 289 contain modules of authentication support 1271 (in turn including patient 1273 and healthcare professional 1275 authentications), user registration support 1285 (in turn including registration database 1283), image/sensor data database support 1287, billing module 1277, autosuggestion module 1279 and external server support 1281. The autosuggestion module 1279 and external server support 1281 makes it possible for the user to get advices and suggestions from other interlinked websites, based upon the diagnosis and condition.

Regional healthcare professional servers 1259 consist of image/sensor database 1251, service charges module 1253, healthcare professional registration support 1255 and diagnosis equipments/suggestion/treatment service support 1257. The diagnosis equipments/suggestion/treatment service support 1257 module allows healthcare professionals to interface the regional healthcare professional servers 1259 with external equipments and remote healthcare professional servers 1239.

The remote healthcare professional servers 1239 allow the image/video clip/sensor data to be sent to distant lands where healthcare professionals are able to make diagnosis and mention the priorities necessary in treating them. This saves valuable time on the part of regional healthcare professionals. The remote healthcare professional servers 1239 consist of image/ sensor database 1233, healthcare professional registration support 1231 and diagnosis equipments/suggestion/treatment service support 1235 to enable this to happen.

Figure 13:
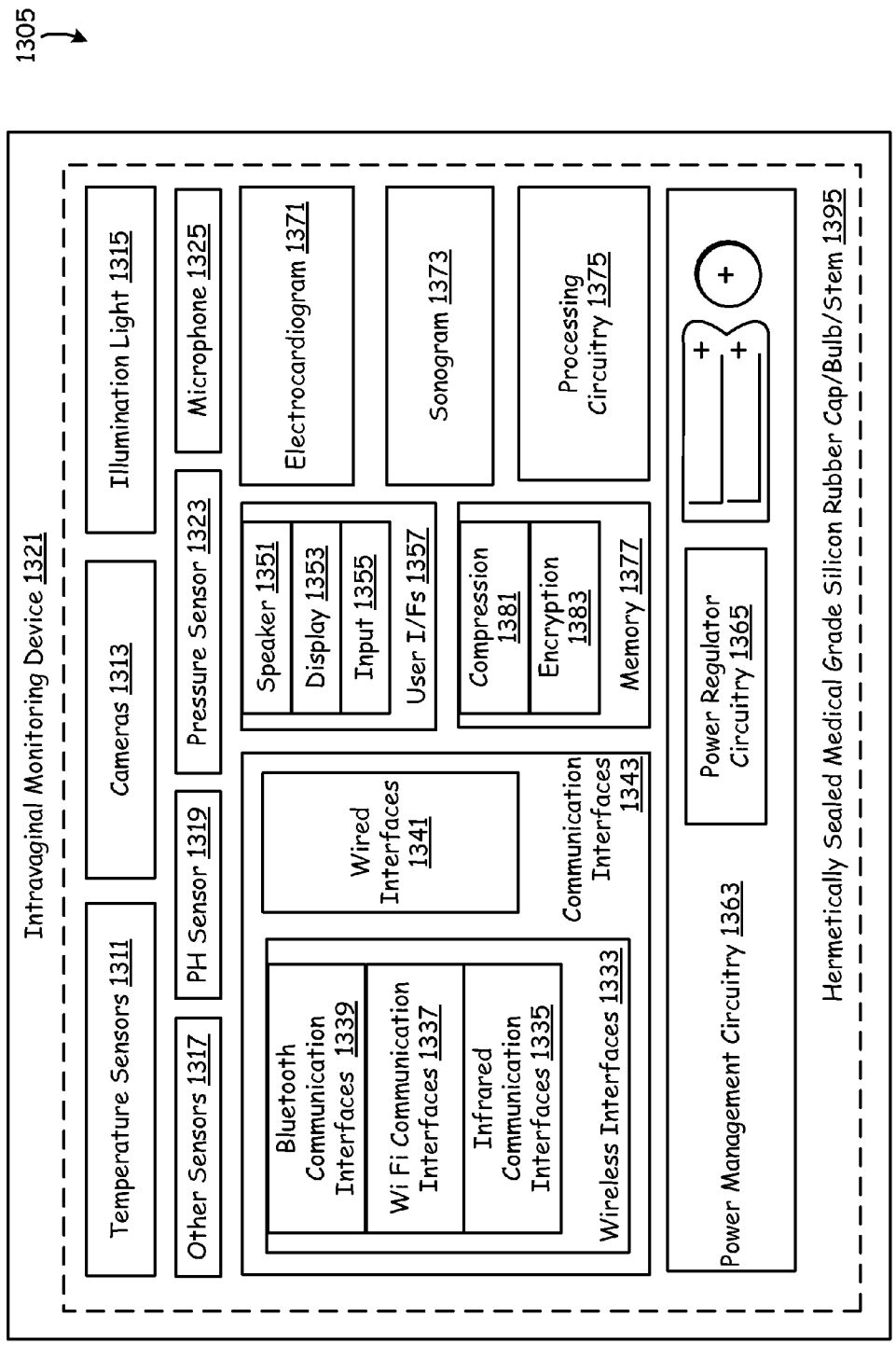
FIG. 13 is a schematic block diagram illustrating the intravaginal monitoring device of the FIG. 11; wherein the intravaginal monitoring device contains wired and/or wireless communication interfaces that enable the intravaginal monitoring device to communicate with the external devices and/or external servers of the FIG. 11, and regional and remote healthcare professional servers of the FIG. 12, via wired/wireless, point-to-point, Internet/Intranet network pathways.

FIG. 13 is a schematic block diagram illustrating the intravaginal monitoring device 1321 of the FIG. 11; wherein the intravaginal monitoring device 1321 contains wired and/or wireless communication interfaces 1333 that enable the intravaginal monitoring device 1321 to communicate with the external devices and/or external servers of the FIG. 11, and regional and remote healthcare professional servers of the FIG. 12, via wired/wireless, point-to-point, Internet/Intranet network pathways.

The components within the hermetically sealed rubber cap/bulb/stem include cameras 1313, illumination light 1315 and temperature sensors 1311, temperature sensors 1311, PH 1319, pressure 1323, microphone 1325 and other sensors 1317, electrocardiogram 1371 and sonogram 1373. These are typical diagnostic components of the intravaginal monitoring device 1321.

Similarly, user interfaces 1357 include input 1355, display 1353 and speaker 1351 units. These interfaces provide the user some control over the functionalities of the intravaginal monitoring device 1321. Moreover, the components within the hermetically sealed rubber cap/bulb/stem also include processing circuitry 1375 and memory 1377, communication interfaces 1343 (that include wired 1341 and wireless 1333 interfaces), and power management circuitry 1363 (that includes power regulator circuitry 1365 and batteries of various types).

The memory 1377, in some embodiments, may include some preprocessing modules, such as compression 1381 and encryption 1383, to save storage space and to secure the data stored, respectively. The wireless interfaces 1333 may include one or more of Bluetooth communication interfaces 1339, WiFi communication interfaces 1337, and infrared communication interfaces 1335.

FIG. 14 is a schematic diagram illustrating an exemplary snapshot of the web browser page 1405 provided to the patient or user, by the external (supporting) servers of the FIG. 11. The illustration depicts a webpage 1405 that is typically used by the users (who are the users of the intravaginal monitoring device), to upload, transfer to healthcare professional systems and/or share with others (the images/video clips/sensor data) and possibly to get some recommendation/treatment/assistance/advice for a fee or free of cost.

The webpage of the IMD (Intravaginal Monitoring Device) support server is indicated in the depiction as a webpage from www.imdsupport.com 1421. The webpage 1405 of a client's (or user's) browser 1495 provides homepage, about page, contact us and FAQ (frequently asked questions) links 1451 at the top and also provides a language 1445 pull down menu 1449 to choose from. On the left side is a link pertinent to the user's account 1441, where the user may enter all of the necessary personal data. A user can activate an archival storage module to save her data in a secure storage medium during the course of her lifetime and be able to have a single point of reference to retrieve this data, e.g. this is particularly useful where jobs arc changed requiring geographical relocation. In a variant, a single archival source is provided, notwithstanding the user's whereabouts overtime that readily provides valuable baseline and tracking data about a female's organs, events in her life, and the like.

In another window 1493 (where a message such as: "Use Upload Button to Upload Files. Select Date/Time and File Name to View Images." may appear), the user is allowed to upload 1455, 1457 the images/video clips/sensor data or watch (Go To Date 1459, 1461) the images/video clips/sensor data from those that are listed in a separate listing 1497. A separate image display window 1411 may show a small image/data (that can be enlarged) of the selected image/video clip/sensor data to be observed by the user. In another variant, the data harvested from the intravaginal device is correlated with event data and image data taken external of the device, e.g. photo's of sex partners, photo's taken during the course of a pregnancy, event data from the user's real life, recorded songs or text sung to the being in womb during a pregnancy. Hyperlinks to the various data are provided, and also to data on other websites to construct a meaningful time line of events associated with data about events harvested from the females life. In another variant, where an external patch is provided with a still or video camera assembly, the assembly can be used to record events in the birthing theater external to intravaginal monitoring device, e.g. the actions of medical professionals, the emotions being experienced by the birthing mother, the infant's first sounds and appearance as it comes out of the birth canal, the emotions being experienced by the father, etc. This data is correlated to the intravaginally harvested device. As is appreciated a electronic record of the birth both physiological and external is created. This is used to as evidence in a court to defend the actions of healthcare professionals, and to reconstruct the protocols used around the birth.

Figure 15:
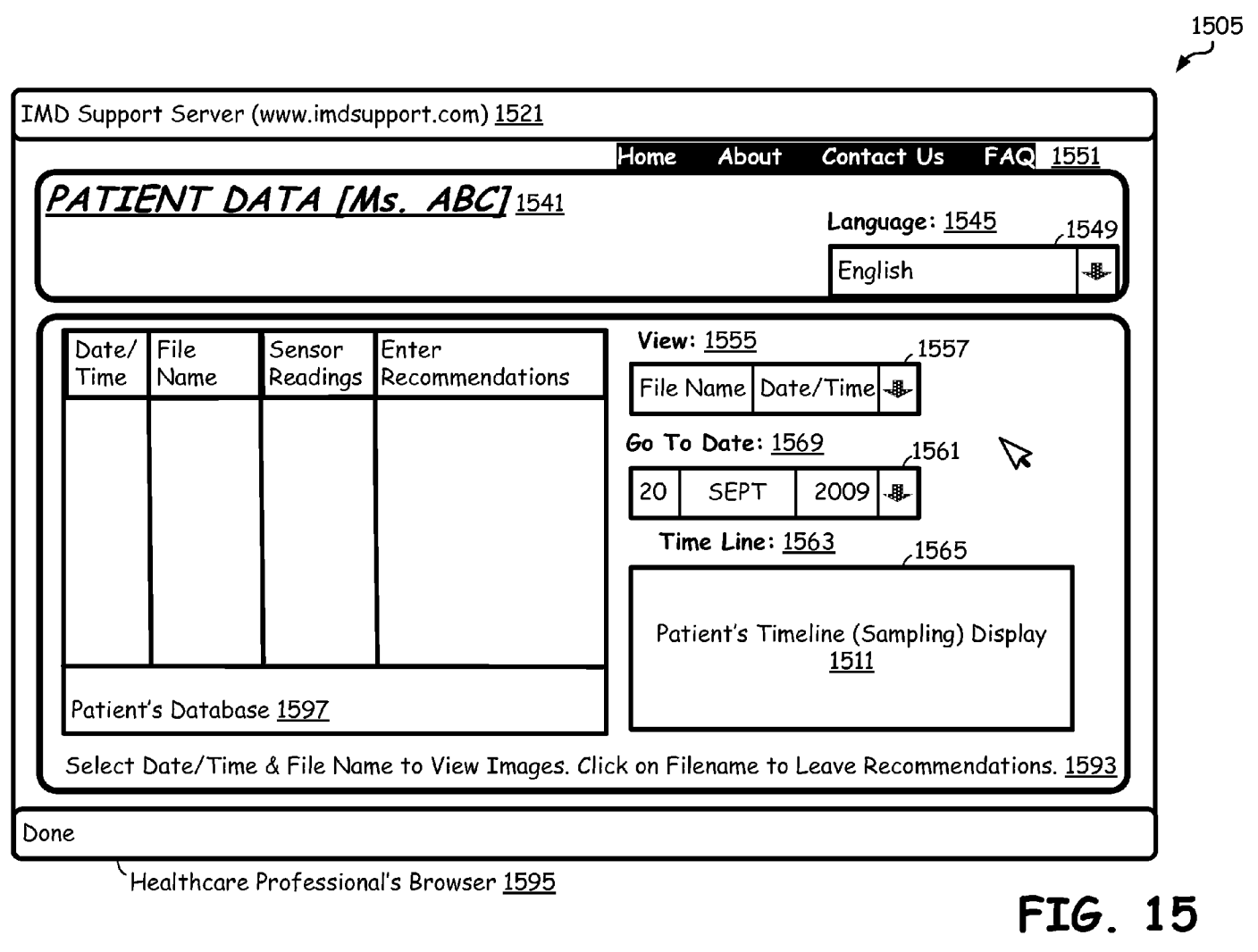

FIG. 15 is a schematic diagram illustrating an exemplary snapshot of the web browser page 1505 provided to the regionally or remotely located healthcare professionals, by the external servers (supporting) of the FIG. 11, via the regional and remote healthcare professional servers of the FIG. 12.

Similar to the webpage 1405 of the user, the illustration of a healthcare professional's browser 1595 also depicts a webpage 1505 that is typically used by the healthcare professionals (who are providing treatment to the users), to view the images/video clips/sensor data and provide recommendation/treatment/assistance/advice for a fee.

The webpage of the IMD (Intravaginal Monitoring Device) support server is indicated in the depiction as a webpage from www.imdsupport.com 1521. The webpage 1505 of the healthcare professional's browser 1595 provides homepage, about page, contact us and FAQ (frequently asked questions) links 1551 at the top and also provides a language 1545 pull down menu 1549 to choose from. On the left side is a link pertinent to the patient's account 1541 is also provided. This information tends to be important in arriving at a conclusion, for the healthcare professional to know the age and nature of a condition.

In another window 1593 (a relevant message to the healthcare professional, such as: "Select Date/Time & File Name to View Images. Click on Filename to Leave Recommendations." may be provided here), the healthcare professional is allowed to view 1555, 1557 the images/video clips/sensor data or watch by "Go To Date 1569, 1561" the images/video clips/sensor data from those that are listed in a separate listing 1597. A separate image display window 1511 may show a small image/data/timeline data (that can be enlarged) of the selected image/video clip/sensor data to he observed by the healthcare professional.

Figure 16:
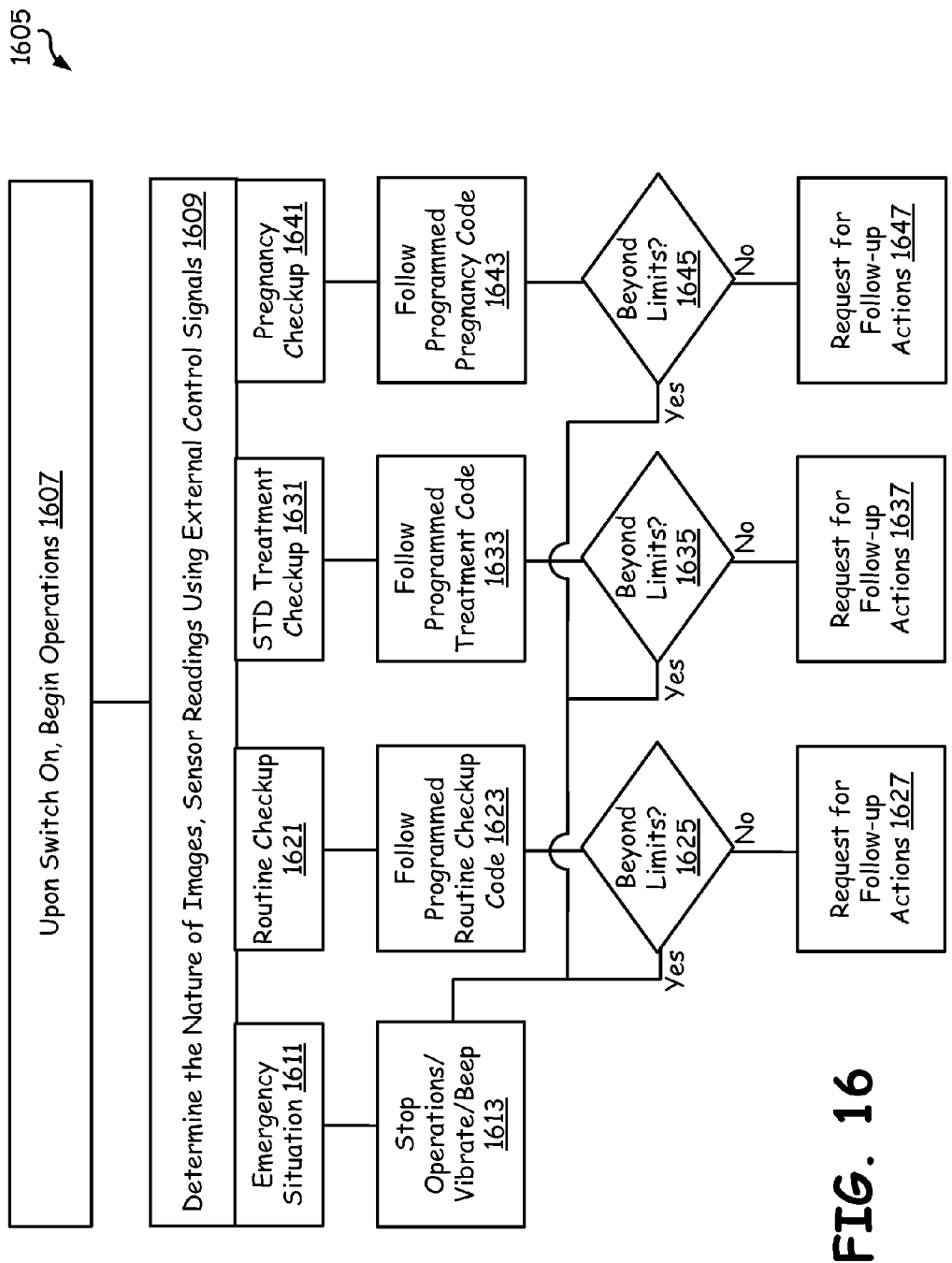
FIG. 16 is a flow diagram illustrating functionality of the intravaginal monitoring device of the FIG. 11, in general.

FIG. 16 is a flow diagram 1605 illustrating functionality of the intravaginal monitoring device of the FIG. 11, in general. The functionality begins at a block 1607 when the intravaginal monitoring device begins operations, upon switch on and placement of the device within the intravaginal channel.

At a next block 1609, the intravaginal monitoring device determines the nature of images (such as color calibrating, normal, microscopic, intervals) and sensor readings (choice of sensors, measurements, frequency or intervals and so forth) to be taken, by using either firmware code or (downloaded) external control signals. Based upon firmware code or (downloaded) external control signals, the intravaginal monitoring device then chooses one of many possible circumstances of the patient such as in blocks 1611, 1621, 1631 or 1641 and chooses one relevant flow paths.

At the block 1611, the intravaginal monitoring device considers an emergency situation such as close to birth of a child or some other painful conditions, based upon the external control signals. At a next block 1613 the intravaginal monitoring device beeps and/or vibrates, by doing so informing the patient to remove the device and possibly transfer the data support server. For example, when a predetermined level of cervical opening has been reached, e.g. the device alerts the user to remove it so as not to interfere with the birthing process or not to obstruct the birth canal. This alert is communicated to one or more nodes on the network, and or by the device itself, alone or in combination.

At the block 1621 the intravaginal monitoring device considers routine checkup and at a next block 1623 the intravaginal monitoring device follows programmed routine checkup code. At a next decision block 1625 the intravaginal monitoring device checks if the readings (images/sensor readings) are beyond normal limits and if yes, follows the emergency situation code of the block 1613. If no, at the decision block 1625, the intravaginal monitoring device requests for the follow up actions at a block 1627. The follow up actions may include removal of the intravaginal monitoring device and transfer of data, or continue to capture images and take sensor data.

At the block 1631 the intravaginal monitoring device considers STD treatment checkup. At a next block 1633 the intravaginal monitoring device follows programmed STD treatment checkup code. At a next decision block 1635 the intravaginal monitoring device checks if the readings (images/sensor readings) are beyond normal limits and if yes, follows the emergency situation code of the block 1613. If no, at the decision block 1635, then, at a next block 1637, intravaginal monitoring device requests for the follow up actions (such as removal of the intravaginal monitoring device and transfer of data, or continue to capture images and take sensor measurements).

At the block 1641 the intravaginal monitoring device considers and can partially or fully conduct one or more protocols associated with a pregnancy checkup. At a next block 1643 the intravaginal monitoring device follows a programmed pregnancy code. At a next decision block 1645 the intravaginal monitoring device checks if the readings (images/sensor readings—such as when the pressure sensor reading is too high and discomforting to the patient) are beyond normal limits and if yes, follows the emergency situation code of the block 1613. If no, at the decision block 1645, the intravaginal monitoring device requests for the follow up actions (such as removal of the intravaginal monitoring device and transfer of data, or continue to capture images and take sensor data), at a next block 1647.

Figure 17:
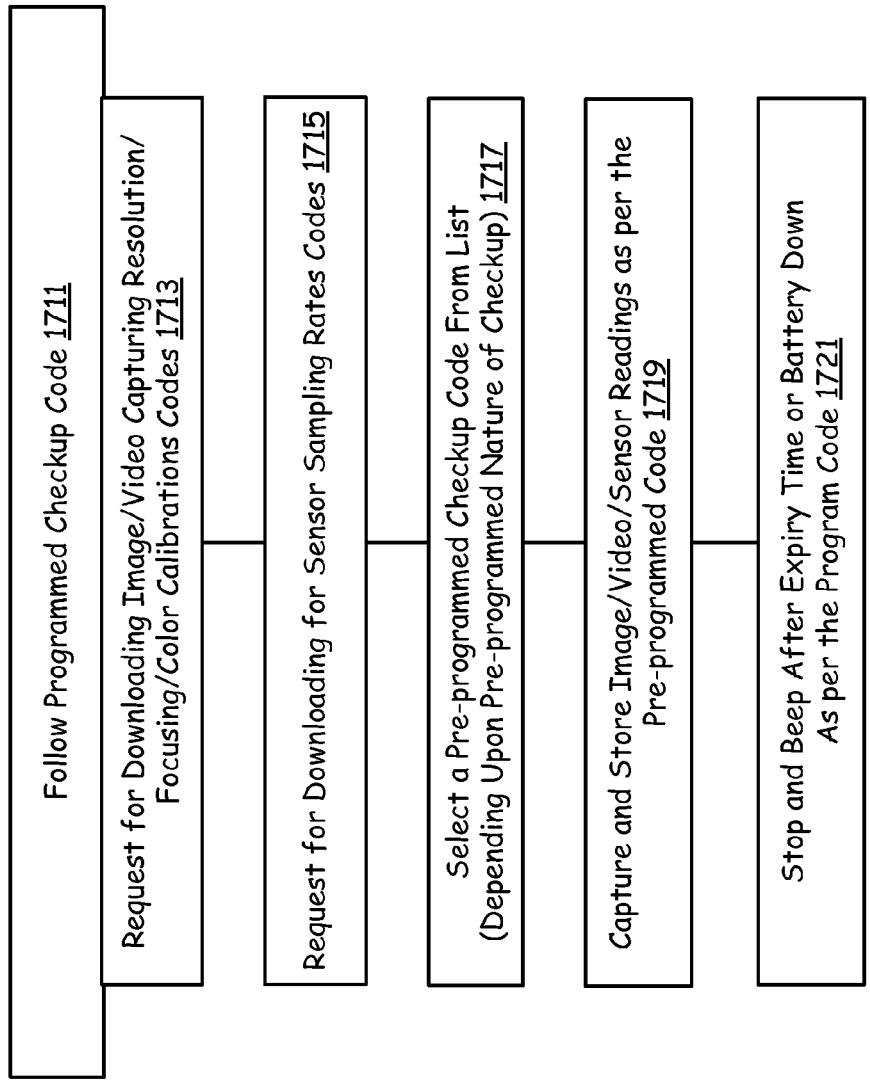
FIG. 17 is a flow diagram illustrating functionality of the intravaginal monitoring device of the FIG. 11; wherein the intravaginal monitoring device follows preprogrammed checkup code.

FIG. 17 is a flow diagram 1705 illustrating functionality of the intravaginal monitoring device of the FIG. 11; wherein the intravaginal monitoring device follows preprogrammed checkup code. The functionality begins at a block 1711 when the intravaginal monitoring device begins to follow programmed check up code (of the blocks 1623, 1633 or 1643 of the FIG. 16).

At a next block 1713, the intravaginal monitoring device requests for downloading image/video capturing resolution, focusing, color calibrations instruction codes. For instance, a healthcare professional may find the resolution to be too low to arrive at a proper diagnosis and may request the support server to pass on program code, to the intravaginal monitoring device, to take images at a much higher resolution, or greater or lesser image capture rate. At a next block 1715, the intravaginal monitoring device similarly requests for downloading of codes for the sensor sampling rates.

At a next block 1717, the intravaginal monitoring device selects a preprogrammed checkup code (possibly, chosen by the healthcare professional) from a list of checkup and treatment codes. At a next block 1719, the intravaginal monitoring device captures and stores image/video clips/sensor data as per the preprogrammed code. This routine data collection, at a predetermined resolution and rates, continues until, at a next block 1721, the intravaginal monitoring device determines to stop the process (depending upon expiry time in the code or upon battery down). This is done by stopping the data collection process and informing the user via beeps or vibrations to remove the intravaginal monitoring device. In one variant, a module on one or more nodes of the devices functions to permit accurate and automated billing of a medical professional's time. For example, data from a patient is communicated the device to a physician's computer or mobile phone. The physician opens the file containing the data and spends 10 minutes reviewing the data, and annotating notes to the file. The system automatically notes the amount of time the physician spent on the file, and integrates this time calculation to a billing system so that the physician's time can be properly billed and reimbursed.

In yet another variant, the device, method and network have a mode of operation that permits annotation and physician commentary, report and or analysis data to be automatically or manually correlated with data harvest from the intravaginal device on one or more nodes of the network. A unitary electronic medical record is created correlated to the intravaginal device data along with suggested courses of therapy or treatment.

Figure 18:
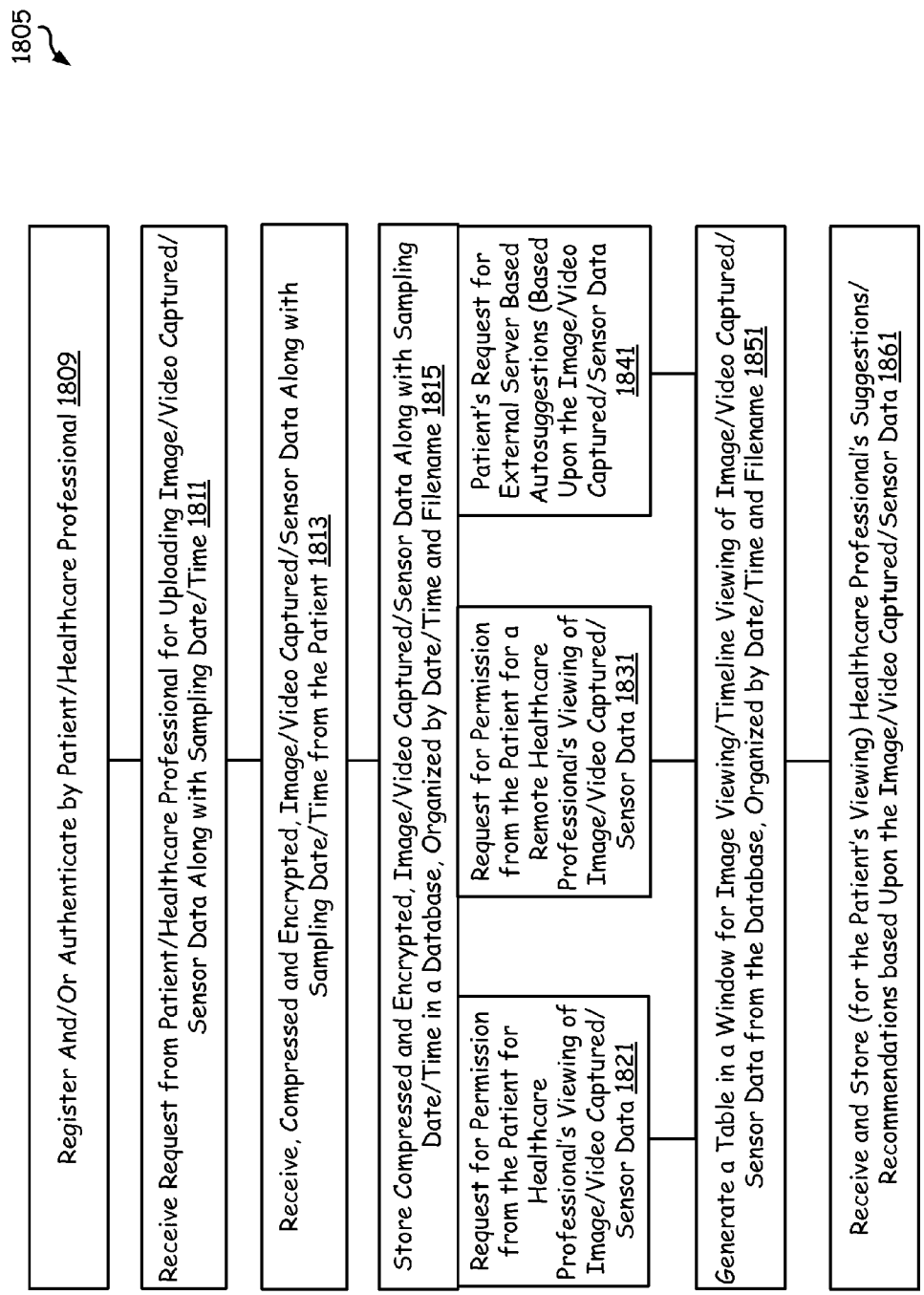
FIG. 18 is a flow diagram illustrating functionality of the external servers of the FIG. 11; in general.

FIG. 18 is a flow diagram illustrating 1805 functionality of the external (support) servers of the FIG. 11; in general. The functionality of the support server begins at a block 1809, when the supporting server allows registering and/or authenticating by a patient and/or healthcare professional. At a next block 1811, the support server receives request from the patient and/or healthcare professional for uploading image/video captured/sensor data along with sampling rates and date/time stamping.

At a next block 1813, the support server receives, compressed and encrypted, image/video captured/sensor data along with sampling date/time from the patient. At a next block 1815, the support server stores the received compressed and encrypted, image/video captured/sensor data along with sampling date/time in a database, organized by date/time and filename.

At next blocks 1821, 1831, 1841 the support server chooses one of many possibilities, based upon the stored patient data and requests. At the block 1821, the support server receives request for permission from the patient for healthcare professional's viewing of image/video captured/sensor data. At the block 1831, the support server receives request for permission from the patient for a remote healthcare professional's viewing of image/video captured/sensor data. At the block 1841, the support server receives patient's request for external server based autosuggestions (based upon the image/video captured/sensor data.

At a next block 1851, the support server generates a table in a window for image viewing/timeline viewing of image/video captured/sensor data from the database, organized by date/time and filename. At a final block 1861, the support server receives and stores (for the patient's viewing) healthcare professional's suggestions/recommendations based upon the image/video captured/sensor data.

In another variant, the intravaginal device, method network and mode of operation harvests and collects data that is used in combination with DNA data related to paternity testing to assist in the identification of a father. By way of example, data entered into onto one or more nodes of the network regarding sexual activity, partner identification information, ejaculation information, sperm in vagina data, are correlated to potential father candidate information if there are a pool of potential candidates. Conception time data and other pregnancy related data are analyzed to select candidates from the pool. Paternity is then conclusively determined by a DNA paternity test, in combination with data from the device, and or other nodes of the intravaginal device network.

Figure 19:
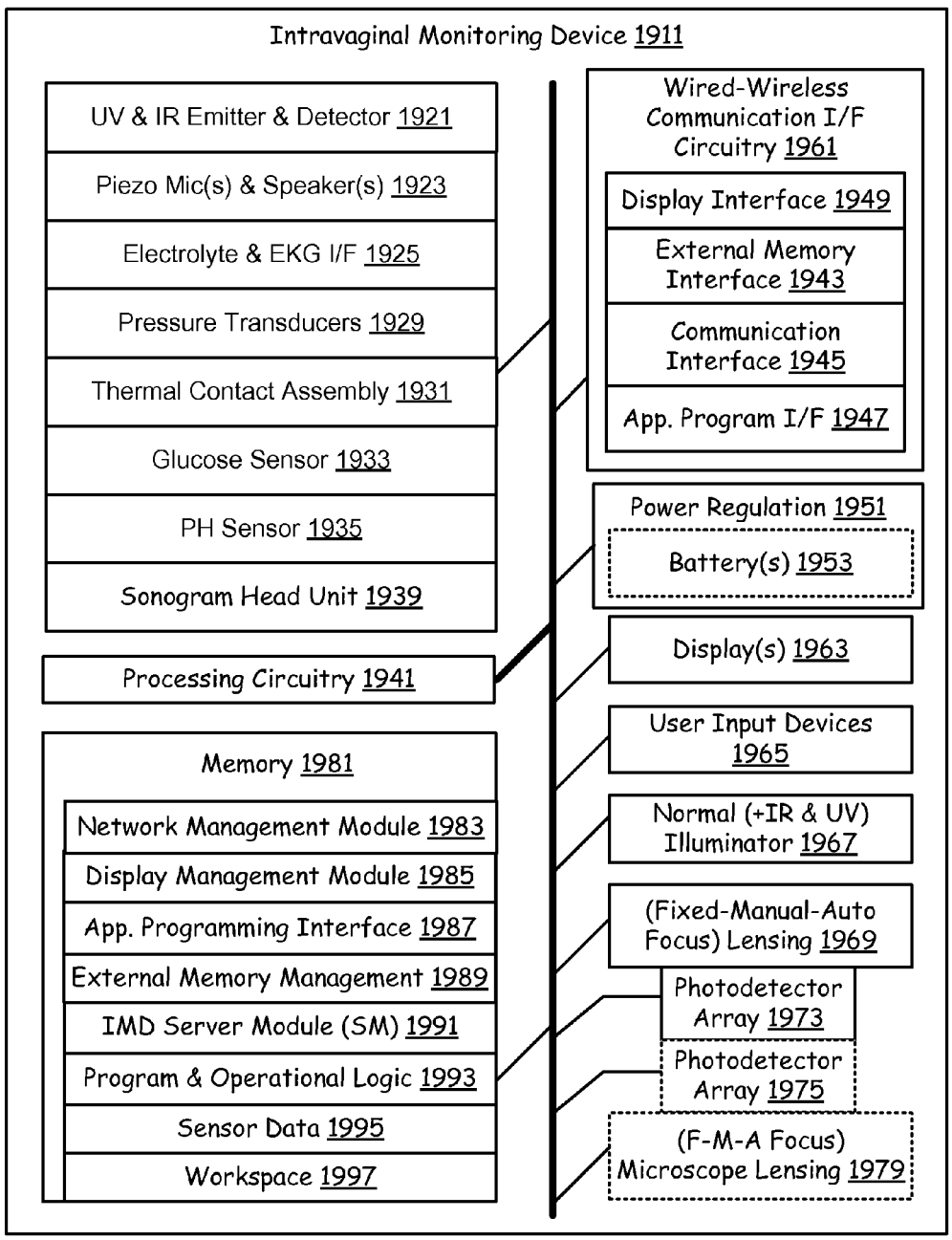
FIG. 19 is a schematic diagram illustrating the components of the intravaginal monitoring device of FIG. 1b (that may be found in exemplary intravaginal monitoring devices such as those found in FIGS. 1-5)

FIG. 19 is a schematic diagram illustrating the components of the intravaginal monitoring device of FIG. 1*b*. The intravaginal monitoring device 1911 contains wired and/or wireless communication interfaces 1961 as well as firmware and program & operational logic codes 1993 that makes it possible for the intravaginal monitoring device 1911 to communicate with the local external electronic devices as well as receive control signals via (immediate) external electronic devices. Moreover, the intravaginal monitoring device 1911 also contains memory 1981, processing circuitry 1941, displays 1963 and user input devices 1965. The memory 1981 additionally contains network management module 1983, display management module 1985, application programming module 1987, external memory management module 1989, IMD server module (SM) 1991, sensor data 1995 and workspace 1997.

Firmware and program & operational logic codes 1983 allow the intravaginal monitoring device 1911 to perform in accordance with specific logic that includes: (a) Receiving and/or executing instructions, in case of wearable intravaginal monitoring device 1911, as to when to switch on and off functionality on the device, when and at what points in time to take images/video clips/sensor data, and at what interval they should be taken; (b) Receiving and/or executing instructions to vibrate/beep, and then, switch off and transfer data to an external device or external servers (such as after enough data to make diagnosis has been taken and it is time to switch off until some other time or in emergency situations such as sometime before delivery of a baby); (c) Receiving and/or executing instructions that involves exceeding limits in cases of sensor data; and/or (d) Monitoring the battery operations and informing the user to recharge batteries, if need be; and so forth.

The sensors and devices that are incorporated into the intravaginal monitoring device 1911 are include components of one or more of: (a) UV and IR emitter and detectors 1921, to monitor temperature; (b) Piezo microphones and speakers 1923, to monitor heartbeat sounds of fetus, for instance; (c) Electrolyte and EKG interfaces 1925, to take electrocardiogram graphs of heartbeat of a fetus, for instance; (d) Pressure transducers 1929, to make pressure measurements within the intravaginal channel, to monitor dilations, for instance; (e) Thermal contact assembly 1931, to take temperature measurements in cases of wearable intravaginal monitoring device 1911, for instance; (f) Glucose sensor 1933, to take glucose measurements; (g) PH sensor 1935; and/or (h) Sonogram head unit 1939.

In all of the above-mentioned sensor cases, a processing circuitry 1941 executes, as mentioned above, the operational logics, and takes measurements at appropriate intervals and also verifies if the limits are exceeded and precautionary actions should be taken. Other components of the intravaginal monitoring device 1911 depicted include normal (infrared and ultraviolet) illuminators 1967, fixed-manual-auto focus lensing 1969, a bunch of photodetector arrays 1973, 1975 (or one or more arrays positioned at predetermined locations on the device) and fixed-manual-auto focus microscopic lensing 1979. The wired and wireless communication interface circuitry 1961 also contains: (a) Display interface 1949, to support on screen displays on external monitors, for instance (on a smart phone or other mobile communications device, e.g. two way); (b) External memory interfaces 1943, to interface with external computers and deliver the memory contents; (c) Communication interface 1945; and/or (d) Application program interface 1947, alone or in combination.

Although the intravaginal monitoring devices 1911 shows a variety of basic types of functionalities, a variety of other intravaginal monitoring devices 1911 may also be built with all of those functionality or some portions of them, still others may also be built with further functionalities, such as having more sensors, more photo sensor arrays, or illuminators and so forth.

The intravaginal monitoring device 1911 is used to gather sensor information from the variety of sensors illustrated when the intravaginal monitoring device is at partially inserted into the vaginal channel. For example relating to an imager (i.e., the photodetector array 1973, the processing circuitry 1941 receives user input from the user input devices 1965 and responds by (i) delivering power from the batteries 1953 to at least one of the illuminators 1967, and (ii) producing a control signal delivered to the photodetector array 1973 directing that imager data (still images and/or video data) is to be captured. The photodetector array 1973 responds by capturing reflections of the illumination from the target area (e.g., a cervix), and delivers such imager data captures to the processing circuitry 1941. Also, in addition to of performing the above behavior in response to the user input, the processing circuit 1941 can also do so in response to control signals received via the communication interface 1945 from external devices. Although described in reference to the photodetector array 1973, such operations performed by the processing circuitry 1941 apply equally to all other sensors of the IMD 1911.

The processing circuitry may a) send the imager data (or a processed version thereof) to the display 1963; b) store the sensor data along with previously captured imager data within the sensor data 1995 of the memory 1981; c) forward the captured imager data via the communication interface 1945 (in real time during the capture process or otherwise) to external supporting devices; d) pre-process the imager data to produce measurement information for use in the above a-c; and e) perform at least a portion of the analysis engine functionality. Whether or not the processing circuitry 1941 performs each element a-e above depends on the particular configuration of the IMD 1911, and may vary pursuant to configurable modes of setup that is maintained by the operational logic 1993. Such modes can be set via the user input devices 1965 or via control signals originating, for example, from an external supporting computing device via the communication interface 1945. Although described in reference to the imager data captured by the photodetector array 1973, such operations performed by the processing circuitry 1941 apply equally to all other sensor data captured by the various other sensors of the IMD 1911.

Thus, the IMD 1911 can operate in an independent mode and under control of the processing circuitry 1941 pursuant to the program and operational logic 1993 within the memory

1981. All control signaling in such mode originate within the IMD and, at times, in response to the user input devices 1965. However, the IMD 1911 as shown can operate in a dependent mode wherein various control signals originating from other supporting devices outside of the IMD 1911.

Switching between independent and dependent modes can occur automatically or require further control signals that direct the switch. For example, in one mode of operation (via configuration or setup), the IMD 1911 begins operating in the independent mode. During such independent operations, an external control signal is received via the communication interface 1947. In response to the receipt, the IMD 1911 enters a controlled mode to carry out the underlying task. After such task is completed, the IMD 1911 returns to the independent mode to continue locally directed operations. Alternatively, the IMD 1911 can be placed in a slave mode wherein no functionality is performed without direction from externally originating control signals. That is, the IMD 1911 can wait (e.g., in a low power, idle state) for external control signals. Upon receipt, underlying procedures are carried out and, once completed, the IMD 1911 returns to the idles state awaiting further instructions (i.e., awaiting further control signals from an external supporting device).

The program and operational logic 1993 (of the memory 1981) consist of operating instructions that direct the processing circuitry 1941 in carrying out the various independent and dependent modes of operation. Moreover, the program and operation logic 1993 defines processes for the selection from the plurality of modes and switching there between. As mentioned, such definition involves, for example, responding to the user input devices 1965 and to incoming control signals from external supporting computing devices. In addition, the IMD 1911 can be placed in various initial modes of operation (either via the user input devices 1965 or via externally originating control signals) in advance of insertion or at any time thereafter by, for example, setting parameters within the memory 1981 that are used to configure the operating instructions of the program and operational logic 1993 for use by the processing circuitry 1941.

Thus, the program and operational logic 1993 may have a plurality of operational procedures from which a user of the IMD 1911 or a user of a supporting external device can select and configure. Some of the operational procedures may be tuned to service particular physiological aspects of the specific reproductive system under service. One procedure, for example, might involve using a first type of illuminator and corresponding imager, while another might involve a different group of sensors entirely and so on.

Figure 20:
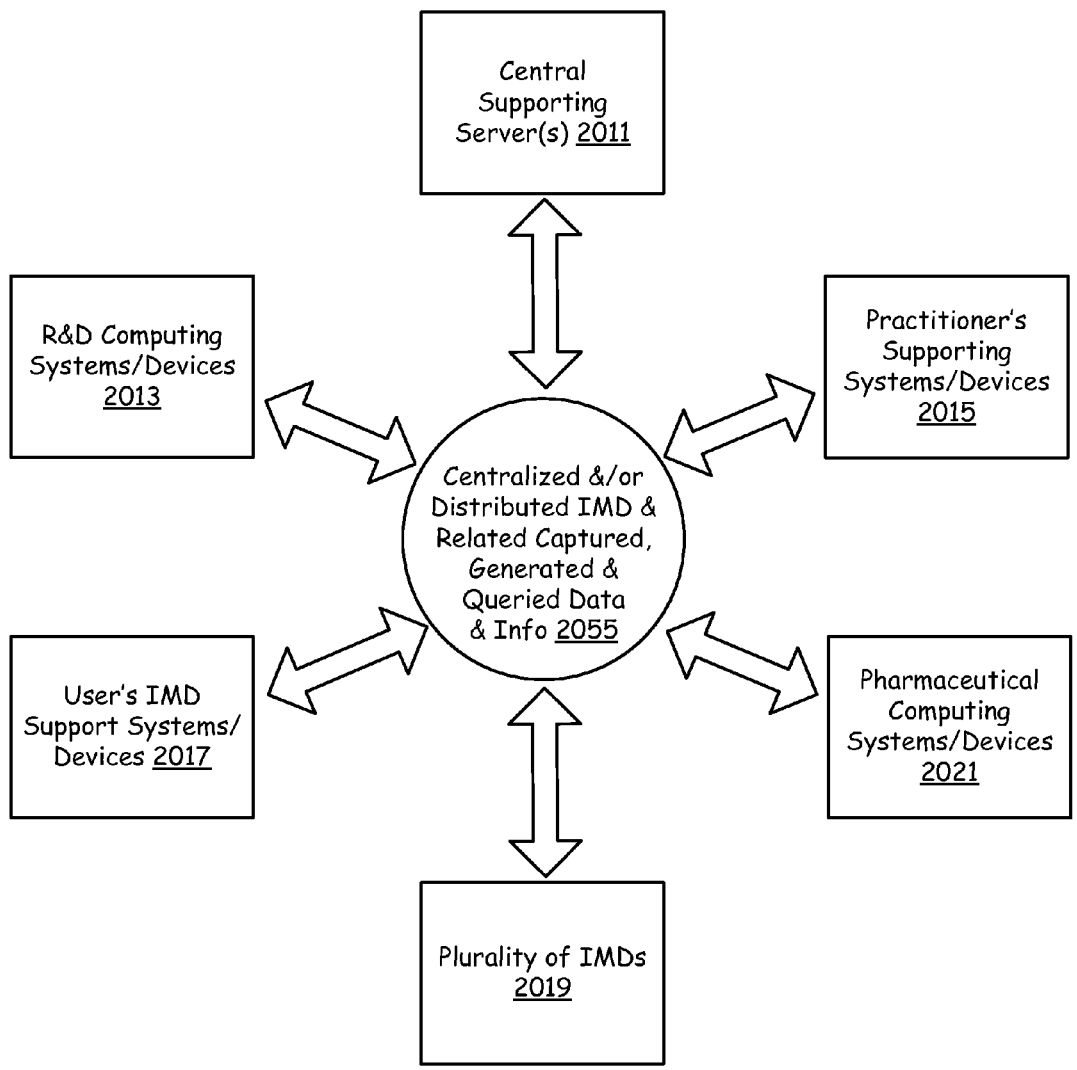
FIG. 20 is a schematic diagram illustrating data flow between intravaginal monitoring device and various systems or devices within the supporting network infrastructure.

FIG. 20 is a schematic diagram illustrating data 2055 flow between each of the plurality of intravaginal monitoring devices 2019 and various systems or devices 2011, 2013, 2015, 20120, 2021 within the supporting network infrastructure. Within the supporting infrastructure, there are various entities such as the 2011, 2013, 2015, 2017, 2021, all of which in a centralized or distributed form hold sensor data (sensor information/query information) from a plurality of intravaginal monitoring devices 2019. Also note that each IMD of the plurality of IMDs 2019 is used to monitor a corresponding one of a plurality of female reproductive systems under service. The In addition, the data/information 2055 also contains data generated via queries, as remedies to various reproductive health related issues or as data collected from auxiliary devices (such as blood pressure, heart rate, blood chemistry, physiological parameter inputs), R&D systems/devices inputs 2013, user IMD support systems/devices 2017, practitioner's supporting systems/devices 2015, pharmaceutical computing systems/devices 2021 and central supporting systems 2011 (or in another variant distributed computing systems including but not limited to cloud networks).

Each of these entities is responsible for dissemination of information/data 2055 and they flow with permission from the respective entities 2011, 2013, 2015, 2017, 2021, 2019 in an encrypted form. These data or information flow in turn assist R&D systems/devices inputs 2013 develop new medicines, user IMD support systems/devices 2017 to take care of the data and avail user forum suggestions and recommendations, practitioner's supporting systems/devices 2015 to provide treatments to the users of IMD 2019, pharmaceutical computing systems/devices 2021 to develop or recommend medicines and central supporting systems 2011 to possibly govern and control all of the movements of data and information in a secured manner.

The supporting devices, e.g., the devices 2011, 2013, 2015, 2017, 2021 establish communication with each of the plurality of IMDs 2019, for example, to retrieve sensor data therefrom. Such retrieved data can be stored, analyzed (analysis engine functionality) and displayed along with any reproductive system status generated. The communication between such supporting devices can be direct point to point links or involve network routing, both via wired and/or wireless infrastructures. The sensor data retrieval and storage can be repeated to cover the many sessions (e.g., insertion sessions) carried out by the each of the plurality of IMDs 2019. The display presented can illustrate differences by merely simultaneously presenting data from, for example, a first session and a second session that is perhaps gathered weeks later. Moreover to assist in detecting the differences, analysis engine functionality can be applied and resulting output can be also presented so that a viewer can easily and fully appreciate the underlying changes. Such presentations may involve historical tracking of features, overlays, highlighting, etc.

Figure 21:
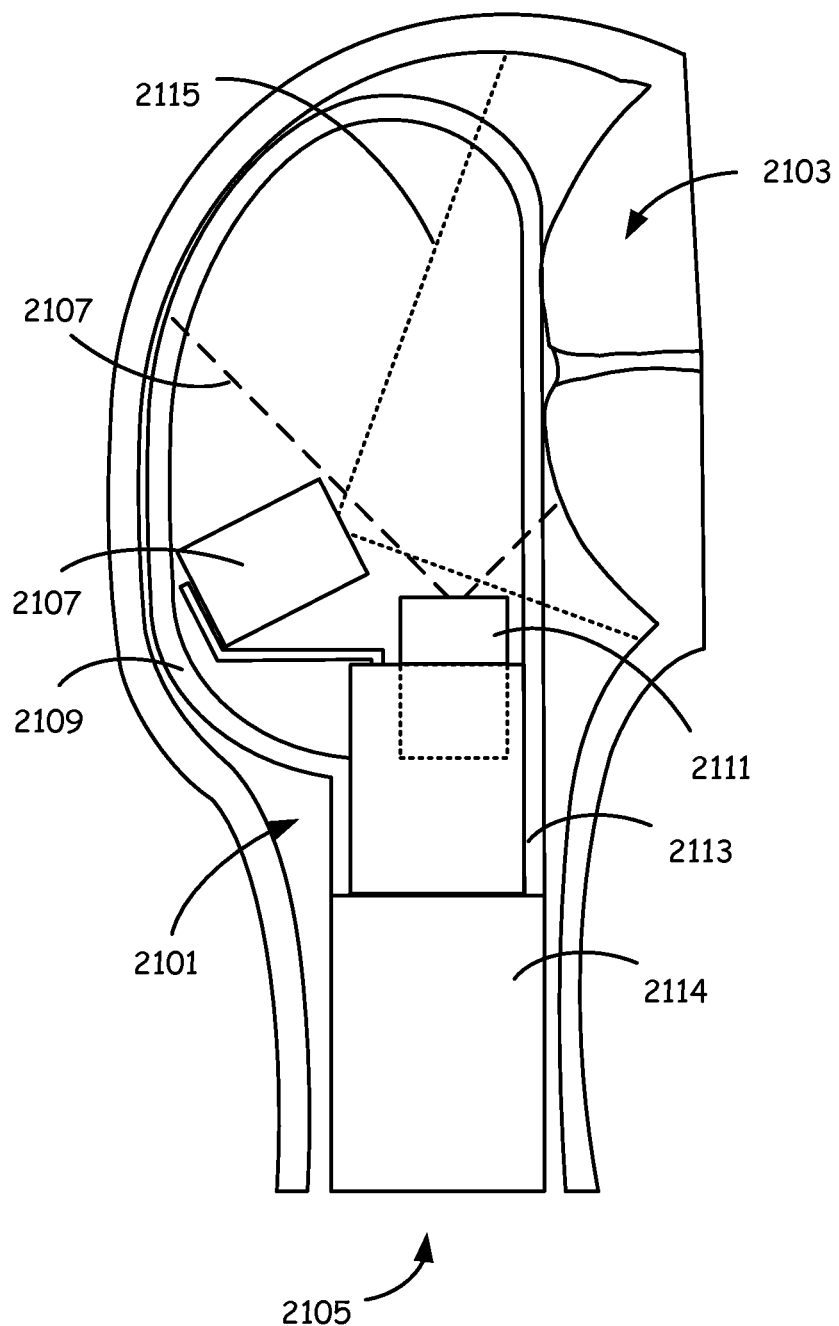
FIG. 21 is a cross-sectional diagrams illustrating one of many possible variations in dimensions, contour, and orientations, i.e., form factors, of a cap and optics assembly of an IMD sized to correspond to various "form factors" of intravaginal and cervical regions. Therein, the IMD is inserted via a mostly axial direction of a vaginal channel.

FIG. 21 is a cross-sectional diagrams illustrating one of many possible variations in dimensions, contour, and orientations, i.e., form factors, of a cap 2109 and optics assembly 2113 of an IMD 2105 sized to correspond to various "form factors" of intravaginal and cervical regions. Therein, the IMD 2105 is inserted via a mostly axial direction of a vaginal channel 2101. Within the vaginal channel 2101 at a mostly radial angle therein, a cervical region 2103 is illustrated. The insertion of the IMD 2105 proceeds until the cap 2109 falls within an area near the cervical region 2103.

The insertion process may benefit from visual guidance of the process via the display of live imager data on an associated display (not shown), and wherein the live imager data is captured by the mostly axially oriented imager 2111. When reaching the illustrated position, the cervical region 2103 falls within a field of view of a mostly radial imager assembly 2107. The mostly radial imager assembly 2107 can thus be used to provide further imager data for a more detailed evaluation of various aspects of the cervical region 2103.

That is, the imager assembly 2111 captures only a portion of the cervical area, but such capture can be used: a) to assist in the guidance process by allowing the user to find and target the cervical region 2103 for image and video capture by the imager assembly 2111; b) along with the image and video capture from the imager assembly 2107 to construct a panorama, 3D information, etc.; c) to support analysis and viewing of other artifacts, events or conditions outside of the cervical region 2103 but within the vaginal channel 2101; and d) to support pre-processing measurements of the cervical region 2103 such as the height, length, width, etc., of the cervix or associated cervical opening portions of the cervical area—an important indication during pregnancy.

The optics assembly 2113 of the IMD 2105 is inserted within a main housing stem 2114. The optics assembly 2113 supports the imager assemblies 2111, 2107. The cap 2109 may be made with a firm but compressible material (such as silicone rubber) that permits installation, removal and replacement. This may be accomplished by feeding the optics assembly into the inner chamber of the cap 2109. Radial tension of the opening portion of the cap 2109 due to elasticity of the cap 2109 supports at least a partial hermetic seal and mechanical constraint.

As illustrated, the field of view and underling mounting angle of the radial imager assembly 2107 is adequately matched to the illustrated reproductive system's orientation and size. Exemplary fine tuning adjustment, however, might involve one or more of: a) installation of a different sized and shaped optics cap; b) relocating the radial imager assembly 2107 to provide better field of view coverage of the present cervix; c) changing the angle of the radial imager assembly 2107 to provide view more normal to the surface of plane of the cervical region 2103; d) extending or retracting the axial imager assembly 2111 directly (or relatively via use of a longer cap) to (i) minimize having the radial imager assembly 2107 within the field of view of the axial imager assembly 2111, (ii) minimize having the axial imager assembly 2111 within the field of view of the radial imager assembly 2107, and (iii) attempting a better lateral image of the cervical region 2103 by relocating the axial imager assembly 2111.

Moreover, further imager assemblies (not shown) could be added to the optical imager assembly, or one of the imager assemblies 2107 or 2111 can be removed. An imager assembly may have integrated illumination lighting and lensing, or other optical elements supporting an imager array installed therein.

The illustrated cap is termed an asymmetric cap as it does not maintain symmetry in the radial direction. Of course fully symmetric caps can be used, such as that illustrated in FIG. 1. the Similarly, to maximize the target coverage area for a field of view 2115 of the imager assembly 2107, the imager assembly 2107 is oriented off center and in the opposite radial direction from that of the cervical region 2103 (the intended target). Similarly, the imager assembly 2107 having a field of view 2107 is positioned with a significant distance to the end of the cap 2115. With such positioning, it is more likely that a reasonably large target coverage area for capturing imager data (by the imager assembly 211) can be maintained. In addition, the extended axial length of the cap 2115 can help in positioning the imager assembly 2107 in its mostly axial position that orients fairly well with the opposing orientation and axial location of the cervical region 2103. If for example, a female's cervical region is much smaller than that illustrated and located closer to the entrance to the vaginal channel, the cap 2109 might be replaced with a longer counterpart. If the cervical region of another female is located in a normal orientation as viewed from the axial direction, a centrally located axial imager assembly only might be used with a symmetric cap of perhaps narrower dimensions.

If installation of a replacement for the cap 2109 is insufficient to address a mismatch between the optical assembly and the desired target, e.g., the cervical region 2103 (which varies greatly from female to female), the optics assembly 2113 might he swapped with another via an electrical and mechanical mating engagement, e.g., a connector within the stem 2114 which matingly engages with a counterpart connector on the base of the optics assembly 2113.

However, note that although larger optics assemblies and caps may be optimal, they may give rise to more difficult and uncomfortable insertion of an IMD. Thus, where these "fitting" processes are limited by comfort and insertion concerns, other cap and optics assembly selections may still prove useful as a compromise under the given reproductive system.

Other aspects of the present invention can be found in additional functionality relating to all of the above embodiments such as that set forth as follows.

The Internet based system, geographically remote intravaginal monitoring devices, each of these devices being communicatively linked to web server and having a mode of operation for tracking the cervical and or vaginal health of a subject. The mode of operation for tracking the cervical and or vaginal health of a subject includes ones for tracking a sexually transmitted disease, for tracking a course of a pregnancy, for tracking the course of a cervical abnormality, for tracking the fertility cycle of a female, for tracking periods of infertility of a female, for harvesting and recording data taken intravaginally, for harvesting data taken intravaginally and harvested extravaginally, for harvesting intravaginal data over the course of female's lifetime, for intravaginal harvesting and recording images taken at least two points in time, and for time and date stamping intravaginally recorded data.

The Internet based system, geographically remote intravaginal monitoring devices further consists of an imager for imaging and tracking clinically relevant changes related to an ovulation event and or the lack thereof to obtain imaged and tracked data, and temperature sensing and tracking capability to obtain sensed and tracked data, the image and tracked data being optionally correlated to the sensed and tracked data to obtain a fertility profile. The Internet based system, geographically remote intravaginal monitoring devices is self powered, and optionally consists of wireless communication capability and a light source; having a mode of operation for presenting the fertility profile on a remote device (the remote device may include a mobile phone, and iPhone™, a consumer electronic product, a netbook, a PDA, a smart phone, a laptop computer, a server, a server communicatively linked to the Internet, and another computer connected to an Intranet).

The Internet based system for determining an ovulation profile of a female may include a self-powered, vaginally insertable electronic module and housing, the housing further consisting an imager for imaging changes in a cervix, and an optional temperature sensor.

The Internet based system further consists of a tracker for tracking changes in a plurality of female cervixes over a period of time; the tracker being located on the device, or optionally at a location remote therefrom.

The Internet based system further consists of: (i) a module for storing temperature data correlated to image data for a plurality of different females to obtain stored health data; (ii) a module for retrieving the stored health data from the Internet based system by a respect female; (iii) a mode of operation for securing the privacy of health data; (iv) a module for alerting the female as to fertility condition; (v) a module for providing a sensory stimulus to a respective female from a node on the system to the respective female's intravaginal device; and (vi) In the step (#v), the sensory stimulus is selected from an audible stimulus, a visual stimulus, a vibratory stimulus, an electrical stimulus, alone or in combination; the stimulus provided directly on the respective female's intravaginal device or a remote device such as an extravaginal electronic device, a mobile phone, and a computer.

In another embodiment, an Internet based system may consist of a plurality of intravaginal imagers for imaging and tracking clinically relevant changes related to an cervical incompetence event and/or the lack thereof for a respective subject, at least some of these imagers wirelessly linked to the abovementioned Internet based system, and a geographically remote storage system communicatively linked to each of the imagers for harvesting and storing data from the imagers. The abovementioned imagers are self powered. The process of determining whether or not a particular female has a cervical incompetence condition involves tracking images taken of a plurality of female cervixes taken within a plurality of vaginas, the females using wearable, self-powered, wireless intravaginal monitoring devices. The process further involves presenting a cervical incompetence profile for a respective female on a remote device, such as a mobile phone, an iPhone™, a smart phone, a laptop computer, a server, a consumer electronic, a server communicatively linked to the Internet, and another computer connected to an Intranet. Then, each of the abovementioned plurality of self powered electronic devices consists of a insertable electronic module and a housing; the housing further conisiting an imager for imaging changes in a cervix, and Internet connectivity, and a mode of operation for determining abnormal changes in the cervix.

The abovementioned Internet based system further consists of: (i) a tracker mode of operation for tracking changes in the cervix over a period of time; the tracker mode of operation being located on the device, or optionally at a location remote therefrom; (ii) a secure mode of operation for protecting the privacy of information; (iii) a notification mode of operation alerting the females as to an event, such as a fertility condition or an incompetence event; (iv) a sensory stimulus (such as an audible stimulus, a visual stimulus, a vibratory stimulus, and an electrical stimulus) mode of operation; (v) an imager for imaging clinically relevant changes related to a sexually transmitted disease event and or the lack thereof to obtain imaged data; and (vi) an optional temperature sensing and tracking mode of operation to obtain sensed and tracked data on the devices; the sensed and tracked data, and imaged data being communicated via a communication link from the devices to one or more remote devices for storage thereon.

The abovementioned Internet based system further consists of tracking the spread of sexually transmitted diseases consists of harvesting STD data from a plurality of geographically dispersed intravaginal monitoring devices harvested data, and communicating the data to an Internet based computer.

The abovementioned Internet based system further consists of a method for determining a sexual health profile of a pool of females with a plurality of wearable, electronic intravaginal monitoring devices, consisting of tracking changes in a cervix of each of the females with the devices to obtain cervix data, optionally tracking changes in the females' body temperatures to obtain temperature data, optionally correlating the cervix data to temperature data to obtain correlated data, and communicating the correlated data over the Internet to a remote device.

The tracking of changes in the female's body temperature further consists of taking an intravaginal temperature reading with the device and then, sending information from the plurality of devices to the remote device (such as a mobile phone, a laptop computer, a server on a network, a cell phone tower, a consumer electronics product, and another medical device), wherein at least a portion of the sending consists of wirelessly sending. The tracking of changes further consists monitoring an event utilizing a monitoring module; the monitoring module being located on the intravaginal device, the remote device, or a combination thereof, and may include one of a precancerous condition monitoring module, a cancerous condition monitoring module, a post treatment condition monitoring module, an STD related monitoring condition module, a physical abnormality monitoring module, an ovulation condition monitoring module, a non ovulation condition monitoring module, a pregnancy condition monitoring module, a non pregnancy condition monitoring module, a menopause monitoring module, and a premenopause monitoring module.

The abovementioned Internet based system further consists of a plurality of intravaginal information capture devices geographically distributed, and each of these capture devices communicating intravaginally harvested data to the Internet. The abovementioned system captures and stores vaginal information, and processing circuitry on each device functions to manage the storage of vaginal information in a memory on the device via the information capture system. The information capture device itself may be a camera or one or more sensors.

The abovementioned Internet based system further consists of a an event monitoring mode of operation, which may include a preconception event, a conception related event, a fertility event, a post conception event, a first trimester event, a second trimester event, a third trimester event, a pre-birth event, a post birth event, a sexually transmitted disease event.

The abovementioned Internet based system further consists of more than one secure communication links, such as a secure mobile wireless network, a secure Intranet, and the Internet via a secure data transfer protocol.

The abovementioned Internet based system, in which the abovementioned events may include an abnormal event associated with a pregnancy, spotting, discharge from the cervix, blood spotting.

The abovementioned Internet based system further consists of a plurality of vagina insertable monitoring devices, each of the devices and/or a remote node on the network consisting of an image processing system, in which one frame taken internally of a subject and at one point in time is compared to another frame taken at a second point in time; whereby the image processing system is used to determine whether a gynecologically or obstetrically relevant event has occurred and or has not occurred. And, the gynecologically or obstetrically event of interest themselves may include one of a color change event, a fluid discharge event, an event associated with an infection, a contraction event, a temperature change event, an event associated with tissue change, an event associated with tissue discoloration, an event associated with the presence of an abnormal fluid within the vagina, an event associated with the presence of a pathogen in the vagina. In addition, the system may include the Internet and an Intranet.

In one of the embodiments, a system for data capture of events within a plurality of vaginas is considered, consisting of a plurality of data capture devices for capturing information while the devices are inserted in the vaginas; the devices each consisting sonic circuitry capable of processing and identifying a heart rate, the heart rate selected from a heart rate of an expectant mother and a heart rate of a fetus in a womb. The data capturing devices may include one of an infrared transmitter and receiver designed to determine and/ or identify one or more physiologically relevant events for each the female and or a being or beings within the wombs of the females. The data capturing devices may consist of one or more piezos, used to identify, quantify, and/or determine data consisting contraction data, and/or any other obstetrically or gynecologically events of interest.

The Internet based system further consists of a plurality of electronic devices for insertion within a plurality of vaginas, each of the devices consisting a contraction tracking system, the contractions being determined optically by the contraction tracking system, and contraction data from a plurality of the vaginas being communicated to the Internet. In the abovementioned system, the frames taken at one time are compared to frames taken at a second point in time by the contraction tracking system.

In one embodiment, the Internet based system for managing multiple pregnancies, consists of a multiplicity of intravaginal electronic monitors inserted within a multiplicity of pregnant females, each of the devices consists of a data capture system for providing useful contraction information using a contraction tracking system (the contractions being determined electrically by pressure contraction measurements, and/or optically by the contraction tracking systems); the monitors communicating the contraction information to a remote device communicatively linked to the Internet.

In one embodiment, the Internet based system for managing multiple pregnancies, consists of a multiplicity of intravaginal electronic monitors inserted within a multiplicity of pregnant females, each of the monitor consisting an information capture system (the information capture system electrically determining an EKG, such as an expectant mother EKG and an EKG of a being within the womb of the expectant mother, and a discriminator for separating the two EKGs); each of the monitors communicating the EKG information to a remote device communicatively linked to the Internet.

In one embodiment, the Internet based system for managing multiple pregnancies, consists of a multiplicity of intravaginal electronic monitors inserted within a multiplicity of pregnant females; each of the monitor consisting a data capture system for providing information about the heart rate of each the pregnant female, and communicating the EKG information to a remote device communicatively linked to the Internet.

In one embodiment, the Internet based system consists of a multiplicity of intravaginal monitoring devices, each of the devices consisting of a data capture system; the data capture system consists of one or more the following, alone or in combination; (1) an infrared system; (2) a system for determining a change in volume of blood flow; (3) a heart rate detector of a being inside the womb of each the pregnant woman; (4) an electronic physiological information detecting patch placed on the stomach of the mother; (5) a data capture mode lasting in the range of 0.25 hours to several months; (6) a mode of operation that looks at streaming video data, analyzes the data to obtain results of the analysis; (7) a physiological data capture mode of operation; (8) a mode of operation effected once a threshold of a value has been met; (9) a warning alert mode, wherein the warning is selected from the group consisting of a warning to the expectant mother and/or father that an abnormal event associated with a pregnancy is occurring or has occurred; (10) a warning concerning about amount of time prior to a birthing event; (11) a warning concerning a gynecological abnormality; (12) a alert concerning a fertility event; (13) a warning concerning an infertility event; and (14) a warning concerning an event associated with an infection.

In one embodiment, the Internet based system, in which one or more commands are directed to an intravaginal monitoring device, the commands actuating or de-actuating a mode of operation of the device; the mode of operation includes: (1) a mode of operation capable of capturing data of events and presenting the data in a chronological manner; (2) a mode of operation that alerts an individual about an insertion time, keeping inside time, and a removal time for the device; (3) a mode of operation that provides an alert that warns a subject that the device has been inserted for too long a period of time or a period of time not long enough, or of a series of possibly detrimental events; (4) a mode of operation that provides a warning, the warning presented visually, audible, and/or by vibration, or a combination thereof; (5) a microphone mode of operation; (6) a direction microphone mode of operation; (7) a GPS mode of operation; (8) a half duplex mode of operation; (9) a full duplex mode of operation; (10) an image capture mode of operation; (11) sonic emitter mode of operation; (12) a sonogram capture mode of operation to monitor a position; the position selected from the fetal position, position of head, position of a fetal foot, an incorrect birthing position, and a correct birthing position; (13) a mode of operation for determining a babies' size of its head, and periodically catching a sonogram shape of the head or the baby; (14) a mode of operation for a daily baby in womb growth rate (in absolute terms, e.g. grams, or in percentage growth rate) and/or providing a histogram or chart tracking the in womb growth rate; (15) a mode of operation for tracking development of a baby in the womb prior to, at full term development, and post normal full term birthing time; (16) a mode of operation for determining ovulation based upon a physiological readings taken by the device; (17) a mode of operation for tracking development of a baby in the womb prior to, at full term development, and post normal full term birthing time; (18) a mode of operation for tracking preconception, conception, post conception, after full term female events; (19) a mode of operation for tracking development of a baby in the womb including a record of the babies' in womb movements, the in womb movements including hand, torso, arm, leg, head and foot movements; (20) a mode of operation for provide a timeline of the entire cycle of female gynecological and obstetric events; (21) a mode of operation for logging the date and or time when the woman has sex; (22) a mode of operation for logging a woman's menstrual period events; (23) a mode of operation for monitoring and/or logging impregnation, a birthing process, and/or a post birthing process; (24) a mode of operation for monitoring the swelling of the cervix events and/or color changes in the cervix events; (25) a mode of operation for recording these events; (26) a mode of operation for monitoring and recording menopause events; (27) a mode of operation for monitoring events of premenopausal woman who want to get pregnant; (28) a mode of operation for predicting and displaying an optimal time for impregnation; (29) a mode of operation for creating a time line of lifetime cervical and vaginal changes; (30) a mode of operation for determining an optimal timing window for insemination or in vitro fertilization; (31) a mode of operation for administration of drugs or sperm from the device; (32) a mode of operation for alerting a subject when to administer a drug and the proper timing of administration of a drug; (33) a mode of operation for administrating a drug to increase fertility and communicating to a user to administer the drug, and/or and external pump (like an insulin pump) to administer the drug and or sperm to a patient, and external pump and related circuitry getting its data and commands from this device or system; (34) a mode of operation for adjusting the drug dosage and administration regimen; (35) a mode of operation for tracking and recording, a heart rate, the heart rate selected from the group consisting of a child's heart rate, a mother's heart rate, and optionally a mode of operation for distinguishing one from the other and presenting same, at a point later in time, in real time, simultaneously on the device or system; (36) a mode of operation and electronics for taking a real time sonogram of a baby in a womb of a subject taken by the device and presented on a remote device, e.g. cell phone, wireless communication enabled television, web enabled television, whereby a husband can sit with wife and see the baby in the womb in real time or at a time delay; (37) a mode of operation providing a graphic user interface; the graphic user interface (GUI)

selected from an expectant mother's graphic user interface, an expectant father's graphic user interface, a hospital administrator's graphic user interface, an obsetrician's, a doctor's GUI, a nurse's GUI, a midwife's GUI; (38) a mode of operation for creating an electronic medical record preconception to post birth for one or a multiplicity of subjects, in womb babies, and post birth families; (39) a mode of operation and electronics for this device or system to communicate its information to a remote device, the remote device including a hospital billing system, a doctor's office invoicing system, a reimbursement system for a national healthcare system, a monitor used traditionally in a birthing center, or a monitor used in a gynecological doctor's office, hospital or clinic; (40) a mode of operation in which a remote device, the remote device including a hospital billing system, a doctor's office invoicing system, a reimbursement system for a national healthcare system, a monitor used traditionally in a birthing center, or a monitor used in a gynecological doctor's office, hospital or clinic, communicates information back to the device that is inserted into a vagina; (41) a mode of operation in which there is two way communication of instructions and data between the device located in the vagina and a remote device; (42) a mode of operation for archiving images from a remote data storage source are communicated to the device inserted into The Internet based system within a vagina and compared to images taken in real time or recently taken, whereby changes in cervical conditions are capable of being determined over the course of user's lifetime; (43) a mode of operation in which predictions are made, the predictions selected from the group consisting of a date and or time to birth prediction, an expected clinical event prediction, a types of therapy needed or desired; (44) a camera mode of operation, an image capture mode of operation for capturing images of the cervix or other vaginal anatomical structure in one, two and or three dimensions; (45) a mode of operation for providing data related to the three dimensional contours of the cervix; (46) a mode of operation to track effacement of cervix; (47) a mode of operation to determine dilation of cervix; (48) a mode of operation to correlate and present data of cervical dilation and cervical effacement, simultaneously, or separately; (49) a mode of operation for baseline capture of internal images of woman's vagina and cervix, and/or physiological parameters at different points in time using the device, system and method of the present invention; (50) a mode of operation for identifying, and/or tracking abnormal growths on a female anatomy, tracking cysts, genital warts, and/or other growths in a females lower body, and reproductive organs, and/or any combination thereof; (51) an electronic medical record mode of operation to digitize this information over the course of a woman's lifetime (premenopausal, post menstrual to post menopausal, or any variant of a period of time there between); (52) a mode of operation in which the device or system detects an abnormal event for a user of the device; (53) a mode of operation for patient scheduling and appointment, identifies which doctor has the earliest appointment available (helps relieve the stress for the patient); (54) a mode of operation in which a user or medical professional loads medical event information about the user, personal information about the user, medical record information about the user, information about the device, e.g. serial number, date of production, model type, information from another device of this type onto a new device, onto the device and system taken from another such device or a remote medical information diagnostic device; (55) a mode of operation for a comparison of archival state of disease or event data with current state of disease or event data; an optional music player and or recorder mode of operation, the music player such as a digital music player, an MP3, MP4 player, a music player playing educational music for a being in a womb, messages sent from the internet from family and friends to child, recording mothers words, songs and text the mother or father are saying and singing to the being while the being is in the womb, digital pictures of the family, mother, and father and other digitally stored information; (56) a one way (in one variant) and (two way) information and instruction flow between the device and a remote device mode of operation; (57) a mode of operation that predicts timing of a birth or birth related event based upon the sensor and or camera input, or external statistical information gathered; (58) a mode of operation that senses fluid discharge, optionally quantifies the fluid discharge, and/or includes one or more fluid sensors; (59) a mode of operation that places date and time stamps fluid discharge events; (60) a mode of operation that time and date stamps fluid discharge events and ranks the events as non problematic or problematic, and optionally sends an alert to a remote device, and/or optionally creates a timeline or chronological record of each the event and the severity of the event; (61) a mode of operation that includes functionality, including one or more of the following features—image stabilization, image tracking, image tracking when device is inside the vagina only; (62) an optical mode of operation for ensuring the location of sweet spot data; (63) a mode of operation for sonic data retrieval, a mode of operation that automatically adjusts for movement of mother due to walking or contractions; (64) a mode of operation that tracks movement of target cervix and device moving together, alone or in combination; (65) a mode of operation that automatically communicates pre-birth information of the mother and child prior to a hospital emergency room computer system, a birthing center emergency room; and (66) a mode of operation that includes a false labor indicator, a mode of operation that includes a spaced out labor indicator, a mode of operation that includes labor and delivery patient management.

In one embodiment, the Internet based system, in which includes a mode of operation and/or features that include, alone or in combination, processing circuitry for processing the data, and (1) a mode of operation for continuously sending high definition video; (2) a mode of operation where the device or components thereof activate if a relevant parameter changes; (3) a mode of operation in which the device sends base image data and difference data to a remote device; (4) a mode of operation in which the device only send data if there are changes in the data; (5) a mode of operation in which the device only sends data if there are clinically significant changes in data; (6) a mode of operation in which the device sends data if there are clinically significant changes to the data; (7) a mode of operation that includes a normal mode of operation, a dock mode of operation, a marry mode of operation, a periodic data harvesting mode of operation, a continuous data harvesting mode of operation, a full time video mode of operation; (8) a mode of operation in which the device automatically figures out its proper positioning and location; (9) a mode of operation in which the device signals by vibration that it is properly oriented; (10) a mode of operation in which the device visually signals it is properly oriented, alone or in combination; (11) a mode of operation that provides secure transfer of data, alone or in combination; (12) a mode of operation that selectively manages or limits delivery of images to authorized remote devices; (13) a mode of operation that automatically transfer data from the device to another preauthorized device upon a command received from the preauthorized device, a mode of operation that includes anti sniffing capability; (14) a mode of operation in which the device that is insertable into the vagina automatically loads software or an application therefrom onto a user's computer and/or a user's mobile phone or other electronic device, e.g. iPod, so that device can communicate and send data thereto, and receive data and instructions therefrom; (15) a mode of operation that tracks an expectant mother's physiological functions; (16) a mode of operation that tracks baby's physiological functions; (17) a mode of operation that provides drug delivery via the device or a remote device in response to data collected by the device such that contractions are slowed down or stopped; (18) a mode of operation that instructs to calm the woman are provided directly by the device (the device has speakers directly thereon and a microphone) or through a mobile phone communicatively linked to the device, whereby the stress on the expectant mother, expectant father, or other parties, a real time remote node to device delivery of instructions mode; (19) a mode of operation that: based on measurements taken from the device, and or based on information coming from outside the unit, the device (or associated remote device) provides a female or others instructions on how to manage the birthing process, the instructions including information, the information selected from the group consisting of a lay down instruction, a relax instruction, a deep breathing instruction, a medical protocol instruction, a push instruction, a hold instruction, a call an ambulance instruction, a call a 911 instruction, a stay off your feet instruction, a bed rest instruction, a medically relevant therapy instruction, a drug use instruction, a psychologically desired instruction, and an instruction to a third party; (20) a mode of operation that store all patients medical information, and optionally feeds doctors and patients information back into the device or remote device; (21) a mode of operation that provides a female's preexisting health condition information back into the device, get sent back and recorded into unit, e.g. hemophiliac, HPV, HIV, Hepatitis B, etc., heart conditions, hypertension, and any other medicals conditions, sex partner parameters, insurance company and coverage information, e.g. policy numbers, patient information, doctor information, billing information, pre-birth screening information, doctor's and patient's medical information is available from this device, and electronic medical records get downloaded into device; (22) a mode of operation that includes GPS electronics and GPS functionality; (23) a mode of operation in which: the device uses a phone's or third party electronics GPS functionality; (24) a mode of operation in which the device provides GPS Information to mobile phone; (25) a mode of operation in which the device or mobile phone communicatively linked thereto tells you where a doctor is located; (26) a mode of operation wherein the device or mobile phone associated therewith tells a doctor where patient is located; (27) a mode of operation that informs an expectant father where wife is located and route being taken by wife, e.g. by taxi or ambulance, to hospital or birthing center; (28) a mode of operation that provides the route in real-time being taken by the mother to a birthing center or hospital so that the father and/or doctor or other medical professional can catch up and meet; (29) a mode of operation that informs the patient where the doctor is located and his or her route to the birthing event in real-time; (30) a mode of operation that informs all of the parties associated with the birthing event know the location of each other and their relative routes to the event; (31) a GPS mode of operation, method and system of any of the claims herein which includes a mode of operation in which the device or husband's cell phone wakes up the husband or a third party and notifies them that a birthing event or other female event is about to occur, and notifies them information, the information selected from the group consisting of the location of the nearest hospital or birthing center, the location of the doctor, the location of medical help, the location of the nearest fire department, information of the best and fastest route to take using the mobile phones GPS system; (32) a mode of operation communicating with a mobile or automotive GPS system regarding the required information, e.g. nearest hospital, etc. and organizes the proper routing of all involved; (33) a graphical representation mode of operation, the graphical representation selected from the group consisting of being in the womb representation, a cervix animation, a progression of cervical dilation animation, a progression of cervical effacement animation, a graphical representation of an cervical abnormality progression over time; (34) a mode of operation and hardware that includes a docking unit or platform, the docking unit or platform including one or more of the following modes of operation, alone or in combination, a mode of operation in which the docking station or platform acts a gateway to another device or to another network; (35) a mode of operation enabling the device to communicate to the Internet; (36) a mode of operation enabling two or more communication interfaces, one to device, one to device beyond device; (37) a control signal mode of operation, in which the control signals are selected from the group consisting of image and sensor analysis control signals, processing control signals in which processing goes on in whole or in part in the device, control signals for controlling one or more cameras on the device, display control signals, data capture control signals, sensor function control signals, control signals turning on or off modes of operation of the device, data delivery control signals, rate of image capture control signals, periodicity of data harvest control signals, length of time of data capture control signals, delivery of data control signals, on device data storage control signals, vibrator control signals, alert control signals, notification control signals, audible control signals, speaker function control signals, music control signals, video control signals, need to reposition the device control signals, length of time of data harvest by the device control signals, control signals that enable a mode of operation of the device, characterization control signals, heart rate data harvest control signals, temperature data harvest control signals, being in womb data harvest control signals, heart rate data harvest control signals, irregular heart rate monitoring control signals, two way communication device from remote device and to device, memory in device management control signals, data transfer from device to remote unit control signals, alone or in combination; (38) a mode of operation that provides for distributed processing of captured data by the insertable device; (39) a mode of operation that, includes one or more of the following, alone or in combination: a communications channel a periodic update of firmware for the device mode of operation, a wireless hotspot enablement of communication with device mode of operation, a cell phone communication mode of operation, an emergency data from device to remote unit mode of operation, an emergency event trigger based alter data transfer mode of operation, a push data out of device to remote unit mode of operation, a pull data of device to remote unit mode of operation, a mode of operation for sending data from the device outside to analysis group of computers, a mode of operation for sending data out of the device to a remote medical specialist or expert computer, location and or specialist medical center computer, a data routing mode of operation to route device data to one or more appropriate specialist hospital, doctor or medical professional for conditions that are developing in real time with a female and or a being in a womb, a push data from device to outside wearable unit mode of operation, a heart rate sensor mode of operation to measure heart rate through an infrared LED and detector, a sensor processing mode of operation, a temperature sensor processing mode of operation, and electronic microbe detecting mode of operation with microbe detecting electronics, an electronic DNA sensor mode of operation, an electronic RNA sensor mode of operation, an optical image sensor mode of operation, an image stream processing mode of operation; (40) the Internet based system removal string mode of operation; (41) the Internet based system removal string mode of operation whereby tension on the removal string activates or deactivates device functionality; a mode of operation that includes, one or more of the following, alone or in combination: (i) timing circuitry mode of operation to provide a time association with captured information within the insertable device and/or external timing mechanism to provide such association; (ii) historic information presentation mode of operation using (#i) above; (iii) a microscope lensing mode of operation, (iv) a manual/auto-focus mode of operation for imaging cervical microbes; (v) software/firmware mode of operation for analyzing (#iii) images to classify bacteria type, and a mode of operation to generate microbe count information; a mode of operation that includes, one or more of the following, alone or in combination: a light emitting diode mode of operation, in which light emission properties from the light emitting diode are managed to obtain a managed emission profile, the managed emission profile selected from the group consisting of an intensity of light emission profile, a color of light emission profile, a wavelength of light emission profile, a time duration of light emission profile, an energy conservation profile by managing emission from the LED to conserve an energy source, and a therapy profile in which emission of light having a microbe reducing effect is provided; a mode of operation or feature that includes, one or more of the following, alone or in combination: a light source emitter, the light source emitter have an emission profile, the emission profile being selected from the group consisting of a the light source emission profile in the light in a visible spectrum, a light source emission profile emitting in the infrared spectrum of light, a light source emission profile in an ultraviolet spectrum of light.

In one embodiment, a network, consisting an intravaginal monitoring device (for determining physiological data of a female) communicates (consisting of communication functionality) with a remote device to present data collected by the intravaginal monitoring device thereon along with advertising data. The remote device may include one of a mobile phone, a smart phone, an iPhone, a consumer electronic product with wireless communication capability, a television with wireless communication capability, and a computer monitor with wireless communication capability. The advertising data may be correlated with the data collected by the intravaginal monitoring device; the advertisement, for example, may include therapy or drug advertising data is provided. Moreover, a method of delivering targeted therapy advertising, consisting of communicating therapy (such as drug therapy) advertising data to an electronic device (the data sent to the electronic device upon detection of a event and/or condition measured by an intravaginal parameter detecting device) is also considered.

In another

The terms "circuit" and "circuitry" as used herein may refer to an independent circuit or to a portion of a multifunctional circuit that performs multiple underlying functions. For example, depending on the embodiment, processing circuitry may be implemented as a single chip processor or as a plurality of processing chips. Likewise, a first circuit and a second circuit may be combined in one embodiment into a single circuit or, in another embodiment, operate independently perhaps in separate chips. The term "chip", as used herein, refers to an integrated circuit. Circuits and circuitry may comprise general or specific purpose hardware, or may comprise such hardware and associated software such as firmware or object code.

As one of ordinary skill in the art will appreciate, the terms "operably coupled" and "communicatively coupled," as may be used herein, include direct coupling and indirect coupling via another component, element, circuit, or module where, for indirect coupling, the intervening component, element, circuit, or module does not modify the information of a signal but may adjust its current level, voltage level, and/or power level. As one of ordinary skill in the art will also appreciate, inferred coupling (i.e., where one element is coupled to another element by inference) includes direct and indirect coupling between two elements in the same manner as "operably coupled" and "communicatively coupled."

The present invention has also been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claimed invention.

The present invention has been described above with the aid of functional building blocks illustrating the performance of certain significant functions. The boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention.

One of average skill in the art will also recognize that the functional building blocks, and other illustrative blocks, modules and components herein, can be implemented as illustrated or by discrete components, application specific integrated circuits, processors executing appropriate software and the like or any combination thereof.

Moreover, although described in detail for purposes of clarity and understanding by way of the aforementioned embodiments, the present invention is not limited to such embodiments. It will be obvious to one of average skill in the art that various changes and modifications may be practiced within the spirit and scope of the invention, as limited only by the scope of the appended claims.

We claim:

1. A method used by a device that is used for self-examination of a user and that can be communicatively coupled with a computing device, the device sized for at least partial insertion into a female reproductive system via a vaginal channel, the method comprising:
   capturing by a first sensor, when the device is at least partially inserted within the vaginal channel, first sensor data relating to the female reproductive system;
   capturing by a second imaging ultrasound sensor, when the device is at least partially inserted within the vaginal channel, second imaging ultrasound sensor data relating to the female reproductive system; and wirelessly communicating at least the first sensor data to the computing device.

2. The method of claim 1, wherein the first sensor is of a different type than the second sensor.

3. The method of claim 1, wherein the first sensor is selected from the group consisting of an infrared detector, a temperature sensor, an imager, a piezo microphone, an EKG sensor, a pressure transducer, a glucose sensor, a pH sensor, an electrolyte sensor, a pressure sensor, a contraction sensor, a nucleic acid related sensor, a protein related sensor, a fluid sensor, a heart rate sensor, a fetal status related sensor, an oxygen sensor, and a brain activity sensor.

4. A device that is used for self-examination of a user and that is used to gather information from a female reproductive system via a vaginal channel, the device comprising:
a single housing sized for at least partial insertion into the female reproductive system via the vaginal channel, the housing having a central axis along the vaginal channel;
processing circuitry disposed in the single housing;
an imager, disposed in the single housing at a non-normal angle with respect to the central axis of the housing, that captures imager data upon receipt of a control signal;
an illuminator, disposed in the single housing, that provides illumination support to the imager upon receipt of illumination power;
a user input mechanism disposed in the single housing;
a battery power system disposed in the single housing; and,
the processing circuitry responding to the user input mechanism by both delivering the control signal to the imager, and causing delivery of the illumination power from the battery power system to the illuminator.

5. A device that is used to gather information from as female reproductive system via a vaginal channel, the device comprising:
a housing sized for at least partial insertion into the female reproductive system via the vaginal channel, the housing being at least partially deformable anctl/gin ballooniess, and the housing having a first portion and a second portion;
processing circuitry disposed in the housing;
a battery power system disposed in the housing;
a first sensor disposed in the housing at a location that supports gathering of first sensor data from the female reproductive system;
communication circuitry, coupled to the processing circuitry, that supports receipt of an external control signal by the processing circuitry, the external control signal originating outside of the housing, and the communication circuitry being disposed in the housing;
memory, disposed in the housing, that is coupled to the processing circuitry, the memory storing operating instructions to be carried out by the processing circuitry;
operating instructions defining a first mode of independent operation and a second mode of directed operation; and,
the processing circuitry selecting the second mode of directed operation in response to receipt of the external control signal via the communication circuitry.

6. The device of claim 5, wherein the external control signal relates to operation of the first sensor, and in which an external control signal activates the second mode of directed operation, the second mode of directed operation being of a different type of mode of operation than the first mode of independent operation.

7. The device of claim 6, wherein the external control signal only originates from a geographically remote server in a supporting system in communication with the device, and, otherwise, in which the device operates independently; and,
in which the device supports functionality of one or more mobile two-way communications devices.

8. A device that is sized for at least partial insertion into a female reproductive system via a vaginal channel, the device comprising:
a housing, the housing being at least partially deformable and ballonless, and the housing having a first portion and a second portion;
a first sensor disposed in the housing at a location that supports gathering of first sensor data from the female reproductive system;
processing circuitry disposed in the housing that receives input;
memory, disposed in the housing, that is coupled to the processing circuitry;
the memory storing operating instructions to he carried out by the processing circuitry, the operating instructions defining at least two operating procedures, the operating procedures being free of the need to compare optical image data to a predefined standard of quality to run; and
the processing circuitry selecting one of the at least two operating procedures based on the input.

9. The device of claim 8, wherein the input received comprises set up information.

10. The device of claim 9, further comprising communication circuitry, and the input being received by the processing circuitry via the communication circuitry.

11. The device of claim 9, further comprising a user interface, and the input being received by the processing circuitry via the user interface.

12. The device of claim 8, wherein a first operating procedure of the at least two operating procedures is designed for a first physiologic purpose, in which a second operating procedure is designed for a second physiologic purpose, and the first physiologic purpose being different from the second physiologic purpose.

13. A method used by a computing device to support interaction between a first sensor device, a second sensor device, and at least one networked supporting network node, the method comprising:
establishing communication with the first sensor device;
at least partially wirelessly receiving the first sensor data from the first sensor device;
establishing communication with the second sensor device;
at least partially wirelessly receiving the second sensor data from the second sensor device; and,
storing the first sensor data and the second sensor data; in which at least the first sensor data is free of optical sexual organ image data; in which the first sensor device captures first sensor data via a first vaginal channel of a first female reproductive system; and, in which the second sensor device captures second sensor data via a second vaginal channel of a second female reproductive system, and in which at least the first sensor device includes a non-normal angle of intra-vaginal implementation for data harvesting.

14. The method of claim 13, further comprising producing display data from the first sensor data, and supporting a plurality of mobile two-way communication device network nodes communicatively linked to the computing device.

15. The method of claim 13, further comprising delivering control signals to the first sensor device, and supporting a plurality of therapy option network nodes based at least in part on one or more of the received first sensor data and/or the received second sensor data.

16. The method of claim 13, wherein the communication established with the first sensor device comprises network communication, and in which the method further comprises: supporting one or more social media network nodes, the one or more social media network nodes having content associated with a female reproductive system condition of the first female reproductive system and/or the second female reproductive system.

17. The method of claim 13, wherein the first sensor data relates to a female reproductive condition associated with the first female reproductive system, and in which the method further comprises: supporting one or more wearable, non-intravaginal, wireless, self-powered, two-way communication device network nodes capable of voice two-way network communication.

18. The method of claim 13, further comprising displaying in a visual working environment representations of at least a portion of the first sensor data and/or at :least a portion of the second sensor data, and in which the method further comprises: supporting a plurality of mobile applications running on self-powered, wireless, mobile two way telecommunications devices, the application being related to a female reproductive condition of the first female reproductive system and/or the second female reproductive system.

19. The method of claim 13, further comprising supporting storage of data associated with the first sensor device, and in which the method further comprises supporting a postpartum network node, the post partum network node utilizing at least a portion of the first sensor data and/or the second sensor data.

20. A method used by a computing device that interacts with one or more monitoring devices, at least a plurality of the monitoring devices having an optical imager and a non-optical imager that captures imager data from a female reproductive system via a vaginal channel, the method comprising:

receiving a first portion of the imager data, the first portion of the imager data having been captured by the optical imager during a first imaging session;

storing the first portion of the imager data;

receiving a second portion of the imager data, the second portion of the imager data having been captured by the non-optical imager during a second imaging session;

retrieving the first portion of the imager data from storage; and providing a visual output based upon at least the second portion of the imager data, in which one or more of the monitoring anal an e of data harvesting and a monitoring device having a housing, the housing being at least partially deformable and balloon-less and the housing having a first portion and a second portion.

* * * * *